US010395440B2

(12) United States Patent
Ricci

(10) Patent No.: US 10,395,440 B2
(45) Date of Patent: Aug. 27, 2019

(54) BATTERY AGNOSTIC PROVISIONING OF POWER

(71) Applicant: NIO USA, Inc., San Jose, CA (US)

(72) Inventor: Christopher P. Ricci, Saratoga, CA (US)

(73) Assignee: NIO USA, Inc., San Jose, CA (US)

( * ) Notice: Subject to any disclaimer, the term of this patent is extended or adjusted under 35 U.S.C. 154(b) by 154 days.

(21) Appl. No.: 15/395,129

(22) Filed: Dec. 30, 2016

(65) Prior Publication Data

US 2018/0009326 A1 Jan. 11, 2018

Related U.S. Application Data

(60) Provisional application No. 62/378,348, filed on Aug. 23, 2016, provisional application No. 62/359,563, filed on Jul. 7, 2016.

(51) Int. Cl.
*H04W 4/80* (2018.01)
*G06F 19/00* (2018.01)
(Continued)

(52) U.S. Cl.
CPC ............ *G07C 5/008* (2013.01); *A61B 5/1171* (2016.02); *A61B 5/1172* (2013.01);
(Continued)

(58) Field of Classification Search
CPC ............. Y02T 10/7005; B60L 11/1838; B60L 11/1824; B60L 11/1816
See application file for complete search history.

(56) References Cited

U.S. PATENT DOCUMENTS 7,181,409 B1 * 2/2007 Murakami .......... B60L 11/1816
  705/5
9,056,556 B1 * 6/2015 Hyde .................. B60L 11/1851
(Continued)

FOREIGN PATENT DOCUMENTS

EP 2693381 2/2014

OTHER PUBLICATIONS

"Battery Health Monitor," Sonora Graphics, accessed Feb. 29, 2016, 14 pages.
(Continued)

*Primary Examiner* — Ronald D Hartman, Jr.
(74) *Attorney, Agent, or Firm* — Sheridan Ross P.C.

(57) ABSTRACT

According to one embodiment, provisioning an amount of power for one or more vehicles can comprise receiving a request indicating a requirement for an amount of power for the one or more vehicles. The request can indicate the requirement for the amount of power for the one or more vehicles individually or in total. A set of management rules can be read from one or more databases. A set of service configuration information and a set of vehicle specific information for the one or more vehicles can also be read from one or more databases. One or more power sources to meet the requirement for the amount of power for the one or more vehicles can be determined based on applying the management rules and using the set of service configuration information and the set of vehicle information and an indication of the determined power sources can be provided.

20 Claims, 13 Drawing Sheets

(51) Int. Cl.

| | | |
|---|---|---|
| *G05B 15/02* | (2006.01) | |
| *G07C 5/00* | (2006.01) | |
| *G06F 16/248* | (2019.01) | |
| *G06F 16/951* | (2019.01) | |
| *G06Q 10/00* | (2012.01) | |
| *G06Q 30/02* | (2012.01) | |
| *G05D 1/00* | (2006.01) | |
| *G06Q 30/00* | (2012.01) | |
| *G07C 5/08* | (2006.01) | |
| *A61B 5/1171* | (2016.01) | |
| *A61B 5/1172* | (2016.01) | |
| *G07C 5/02* | (2006.01) | |
| *G07C 9/00* | (2006.01) | |
| *B60R 11/04* | (2006.01) | |
| *G06F 3/01* | (2006.01) | |
| *G06K 9/00* | (2006.01) | |
| *B60R 1/00* | (2006.01) | |
| *H02J 7/00* | (2006.01) | |
| *G06F 21/32* | (2013.01) | |
| *G06Q 20/40* | (2012.01) | |
| *G06K 19/07* | (2006.01) | |
| *H01Q 21/30* | (2006.01) | |
| *H04B 5/00* | (2006.01) | |
| *H04W 4/04* | (2009.01) | |
| *B60R 25/102* | (2013.01) | |
| *B60W 40/08* | (2012.01) | |
| *B60W 50/08* | (2012.01) | |
| *G08G 1/017* | (2006.01) | |
| *G08G 1/00* | (2006.01) | |
| *G01C 21/36* | (2006.01) | |
| *B60R 25/20* | (2013.01) | |
| *G07B 15/06* | (2011.01) | |
| *G06Q 30/06* | (2012.01) | |
| *G06F 21/62* | (2013.01) | |
| *G06Q 20/32* | (2012.01) | |
| *H04L 29/06* | (2006.01) | |
| *G06K 7/10* | (2006.01) | |
| *H04W 12/02* | (2009.01) | |
| *H04W 12/04* | (2009.01) | |
| *G08G 1/0968* | (2006.01) | |
| *G08G 1/0962* | (2006.01) | |
| *G08G 1/0967* | (2006.01) | |
| *H01Q 1/32* | (2006.01) | |
| *H04W 12/06* | (2009.01) | |
| *G06F 21/31* | (2013.01) | |
| *G06Q 20/10* | (2012.01) | |
| *G06Q 20/14* | (2012.01) | |
| *H04L 9/32* | (2006.01) | |
| *B60L 53/65* | (2019.01) | |
| *B60L 53/66* | (2019.01) | |
| *B60K 35/00* | (2006.01) | |
| *B60K 6/20* | (2007.10) | |
| *B60M 1/00* | (2006.01) | |
| *B60R 11/00* | (2006.01) | |
| *B60L 8/00* | (2006.01) | |
| *G01S 13/93* | (2006.01) | |
| *B60W 50/14* | (2012.01) | |
| *B60L 5/24* | (2006.01) | |
| *B60M 7/00* | (2006.01) | |
| *G08G 1/16* | (2006.01) | |
| *B60L 7/10* | (2006.01) | |
| *B60L 9/00* | (2019.01) | |
| *B60L 53/14* | (2019.01) | |
| *B60L 53/12* | (2019.01) | |
| *B60L 53/80* | (2019.01) | |

(52) U.S. Cl.
CPC ............ *A61B 5/1176* (2013.01); *B60L 53/65* (2019.02); *B60L 53/665* (2019.02); *B60R 1/00* (2013.01); *B60R 11/04* (2013.01); *B60R 25/102* (2013.01); *B60R 25/2081* (2013.01); *B60W 40/08* (2013.01); *B60W 50/08* (2013.01); *G01C 21/36* (2013.01); *G01C 21/3697* (2013.01); *G05B 15/02* (2013.01); *G05D 1/0011* (2013.01); *G05D 1/0088* (2013.01); *G06F 3/011* (2013.01); *G06F 16/248* (2019.01); *G06F 16/951* (2019.01); *G06F 21/31* (2013.01); *G06F 21/32* (2013.01); *G06F 21/6245* (2013.01); *G06K 7/10257* (2013.01); *G06K 7/10316* (2013.01); *G06K 7/10425* (2013.01); *G06K 9/00087* (2013.01); *G06K 9/00832* (2013.01); *G06K 9/00845* (2013.01); *G06K 19/0708* (2013.01); *G06Q 10/20* (2013.01); *G06Q 20/105* (2013.01); *G06Q 20/108* (2013.01); *G06Q 20/14* (2013.01); *G06Q 20/32* (2013.01); *G06Q 20/3224* (2013.01); *G06Q 20/401* (2013.01); *G06Q 20/405* (2013.01); *G06Q 20/4012* (2013.01); *G06Q 30/012* (2013.01); *G06Q 30/0206* (2013.01); *G06Q 30/0208* (2013.01); *G06Q 30/0601* (2013.01); *G06Q 30/0613* (2013.01); *G06Q 30/0625* (2013.01); *G06Q 30/0635* (2013.01); *G07B 15/063* (2013.01); *G07C 5/02* (2013.01); *G07C 5/0808* (2013.01); *G07C 5/0816* (2013.01); *G07C 5/0858* (2013.01); *G07C 9/00563* (2013.01); *G08G 1/017* (2013.01); *G08G 1/0962* (2013.01); *G08G 1/09626* (2013.01); *G08G 1/096775* (2013.01); *G08G 1/096827* (2013.01); *G08G 1/096838* (2013.01); *G08G 1/20* (2013.01); *H01Q 1/325* (2013.01); *H01Q 1/3266* (2013.01); *H01Q 1/3275* (2013.01); *H01Q 1/3283* (2013.01); *H01Q 1/3291* (2013.01); *H01Q 21/30* (2013.01); *H02J 7/0068* (2013.01); *H04B 5/0037* (2013.01); *H04L 9/321* (2013.01); *H04L 9/3226* (2013.01); *H04L 63/0428* (2013.01); *H04W 4/046* (2013.01); *H04W 4/80* (2018.02); *H04W 12/02* (2013.01); *H04W 12/04* (2013.01); *H04W 12/06* (2013.01); *A61B 2503/22* (2013.01); *B60K 6/20* (2013.01); *B60K 35/00* (2013.01); *B60K 2350/2004* (2013.01); *B60K 2350/2052* (2013.01); *B60L 5/24* (2013.01); *B60L 7/10* (2013.01); *B60L 8/003* (2013.01); *B60L 8/006* (2013.01); *B60L 9/00* (2013.01); *B60L 53/12* (2019.02); *B60L 53/14* (2019.02); *B60L 53/80* (2019.02); *B60L 2240/549* (2013.01); *B60L 2240/70* (2013.01); *B60L 2240/72* (2013.01); *B60L 2270/32* (2013.01); *B60M 1/00* (2013.01); *B60M 7/00* (2013.01); *B60R 2011/0003* (2013.01); *B60R 2011/004* (2013.01); *B60R 2300/30* (2013.01); *B60R 2300/804* (2013.01); *B60R 2325/105* (2013.01); *B60W 2040/0809* (2013.01); *B60W 2050/143* (2013.01); *B60W 2050/146* (2013.01); *B60W 2300/34* (2013.01); *B60W 2540/00* (2013.01); *B60W 2540/02* (2013.01); *B60W 2540/04* (2013.01); *B60Y 2200/91* (2013.01); *B60Y 2200/912* (2013.01); *B60Y*

2200/92 (2013.01); *B60Y 2300/60* (2013.01); *B60Y 2302/07* (2013.01); *B60Y 2400/92* (2013.01); *G01S 2013/936* (2013.01); *G08G 1/16* (2013.01); *H04L 2209/80* (2013.01); *H04L 2209/805* (2013.01); *H04L 2209/84* (2013.01); *Y02T 10/7005* (2013.01); *Y02T 10/7072* (2013.01); *Y02T 10/7083* (2013.01); *Y02T 10/7291* (2013.01); *Y02T 90/121* (2013.01); *Y02T 90/122* (2013.01); *Y02T 90/124* (2013.01); *Y02T 90/128* (2013.01); *Y02T 90/14* (2013.01); *Y02T 90/16* (2013.01); *Y02T 90/161* (2013.01); *Y02T 90/163* (2013.01); *Y02T 90/169* (2013.01); *Y04S 30/14* (2013.01)

(56) References Cited

U.S. PATENT DOCUMENTS

| | | | |
|---|---|---|---|
| 2008/0136371 A1 | 6/2008 | Sutardja | |
| 2008/0312782 A1 | 12/2008 | Berdichevsky et al. | |
| 2009/0021385 A1 | 1/2009 | Kelty et al. | |
| 2009/0091299 A1 | 4/2009 | Lin et al. | |
| 2009/0150016 A1 | 6/2009 | Hung et al. | |
| 2009/0210357 A1 | 8/2009 | Pudar et al. | |
| 2010/0235030 A1* | 9/2010 | Xue | B60L 7/12 701/22 |
| 2011/0043165 A1 | 2/2011 | Kinser et al. | |
| 2011/0082621 A1 | 4/2011 | Berkobin et al. | |
| 2011/0302078 A1* | 12/2011 | Failing | B60L 3/00 705/39 |
| 2013/0105264 A1 | 5/2013 | Ruth | |
| 2013/0127416 A1* | 5/2013 | Karner | G06Q 20/102 320/109 |
| 2013/0175974 A1 | 7/2013 | Bassham et al. | |
| 2013/0221916 A1 | 8/2013 | Kelty et al. | |
| 2013/0221928 A1 | 8/2013 | Kelty et al. | |
| 2013/0262067 A1 | 10/2013 | Zhang et al. | |
| 2013/0332015 A1 | 12/2013 | Dextreit | |
| 2014/0184156 A1 | 7/2014 | Sutardja | |
| 2014/0266059 A1 | 9/2014 | Li et al. | |
| 2014/0277887 A1 | 9/2014 | Slattery et al. | |
| 2014/0358367 A1 | 12/2014 | Copeland et al. | |
| 2015/0015376 A1 | 1/2015 | Jenkins et al. | |
| 2015/0042157 A1 | 2/2015 | Chen et al. | |
| 2015/0061897 A1* | 3/2015 | Kees | B60L 11/1846 340/932.2 |
| 2015/0091503 A1* | 4/2015 | Hyde | B60L 11/1803 320/108 |
| 2015/0149221 A1* | 5/2015 | Tremblay | B60L 11/1846 705/5 |
| 2015/0191098 A1 | 7/2015 | Chang et al. | |
| 2015/0202981 A1 | 7/2015 | Chazal et al. | |
| 2015/0231982 A1 | 8/2015 | Li et al. | |
| 2015/0232083 A1 | 8/2015 | Yu et al. | |
| 2015/0239365 A1* | 8/2015 | Hyde | B60L 11/1861 701/2 |
| 2015/0306967 A1* | 10/2015 | Cohen | B60L 11/1846 701/32.3 |
| 2016/0039419 A1 | 2/2016 | Wampler et al. | |
| 2016/0339794 A1 | 11/2016 | Brochhaus | |
| 2017/0088072 A1 | 3/2017 | Curtis et al. | |
| 2017/0217390 A1 | 8/2017 | Curtis et al. | |
| 2017/0282741 A1 | 10/2017 | Birkenbeil | |
| 2017/0309093 A1 | 10/2017 | Feng | |
| 2018/0009321 A1 | 1/2018 | Ricci | |
| 2018/0009327 A1 | 1/2018 | Ricci | |

OTHER PUBLICATIONS

"Battery Management Systems (BMS)," Electropaedia, Woodbank Communications Ltd, 2005, available at http://www.mpoweruk.com/bms.htm, 7 pages.

"Predictive Battery Management for Commercial HEVs," Eaton, Annual Review Meeting, Chicago, IL, Apr. 1, 2015, 13 pages.

"Term Sheet for ETM™ DC2DC Ground Lease and License: Agreement between EV4 and Host Option #2," EV4, accessed Feb. 29, 2016, 3 pages.

Bratus, Sergii, "Implementation of the Licensing System for a Software Product," Apriorit, Inc., Aug. 5, 2010, 15 pages.

Doloca et al., "Floating License Management—Automation Using Web Technologies," Int. J. of Computers, Communications & Control, Dec. 2011, vol. VI( 4) pp. 615-621.

Herron, David, "Renault customers cry foul over battery pack rental terms—Owning the car but renting the pack puts car makers in drivers seat?" The Long Tail Pipe, EV Business, Sep. 28, 2014, available at http://longtailpipe.com/2014/09/28/renault-customers-cry-foul-over-battery/, 18 pages.

Motavalli, Jim, "Electric cars too expensive? Try renting the battery pack instead of buying it," Mother Nature Network, Apr. 16, 2013, 3 pages.

Sultan, Salys, "Floating License Management: A Review of Flexlm," Digital Rights Management Seminar, Software Protection Techniques, Jun. 30, 2006, 26 pages.

Sung et al., "Robust and Efficient Capacity Estimation Using Data-Driven Metamodel Applicable to Battery Management System of Electric Vehicles," Journal of The Electrochemical Society, vol. 163(6), 2016, pp. A981-A991.

Xing et al., "Battery Management Systems in Electric and Hybrid Vehicles," Energies, 2011, vol. 4, pp. 1840-1857.

Official Action for U.S. Appl. No. 15/393,861, dated Aug. 15, 2018 15 pages.

Official Action for U.S. Appl. No. 15/395,254, dated Oct. 18, 2018 12 pages.

Final Action for U.S. Appl. No. 15/395,254, dated May 23, 2019 12 pages.

* cited by examiner

BATTERY AGNOSTIC PROVISIONING OF POWER

CROSS REFERENCE TO RELATED APPLICATIONS

The present application claims the benefits of and priority, under 35 U.S.C. § 119(e), to U.S. Provisional Application Ser. Nos. 62/359,563, filed Jul. 7, 2016, entitled "Next Generation Vehicle"; and 62/378,348, filed Aug. 23, 2016, entitled "Next Generation Vehicle." The entire disclosures of the applications listed above are hereby incorporated by reference, in their entirety, for all that they teach and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

SUMMARY

A provider or seller of a particular service offered to a user can set rules defining management and/or delivery of those services. The provider may be a repair facility, power charging station or facility, a power source exchange station or facility, or fleet manager and the user may be a vehicle owner or operator. For example, a set of rules can be used to manage services related to use of a battery exchange facility for electric or hybrid vehicles. According to one embodiment, instead of a battery centric model for managing power for the vehicle, a battery agnostic model can be used which can allow users to pay on an amp-hour or other basis. This paradigm could be used in conjunction with the licensing of the battery or multiple batteries, except, instead of licensing the battery or batteries, a service provider or licensor can provide whatever battery or batteries are necessary to meet the purchased power demands. For example, in a fleet environment, a service provider or licensor can provide however many batteries are necessary to supply the fleet with sufficient power to operate their vehicles for a total number of miles per year or other period of time.

According to one embodiment, provisioning an amount of power for one or more vehicles can comprise receiving, at a service provider system and over a communications network, a request indicating a requirement for an amount of power for the one or more vehicles. The request can indicate the requirement for the amount of power for the one or more vehicles individually or in total. The service provider system can read a set of management rules from one or more databases. The service provider system can also read a set of service configuration information and a set of vehicle specific information for the one or more vehicles from one or more databases. For example, the set of service configuration information comprises terms of a license agreement. Additionally or alternatively, the set of vehicle specific information for the one or more vehicles comprises information identifying a type of power source used by each of the one or more vehicles. The service provider system can determine one or more power sources to meet the requirement for the amount of power for the one or more vehicles based on applying the management rules and using the set of service configuration information and the set of vehicle information and provide, over the communications network, an indication of the determined power sources.

In some cases, the power sources comprise batteries. Additionally or alternatively, the one or more vehicles can comprise a plurality of vehicles. In such cases, the request can indicate the requirement for the amount of power for the plurality of vehicles in total. For example, the requirement for the amount of power for the plurality of vehicles in total can be expressed in terms of a total distance travelled by the plurality of vehicles.

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Figure 1:
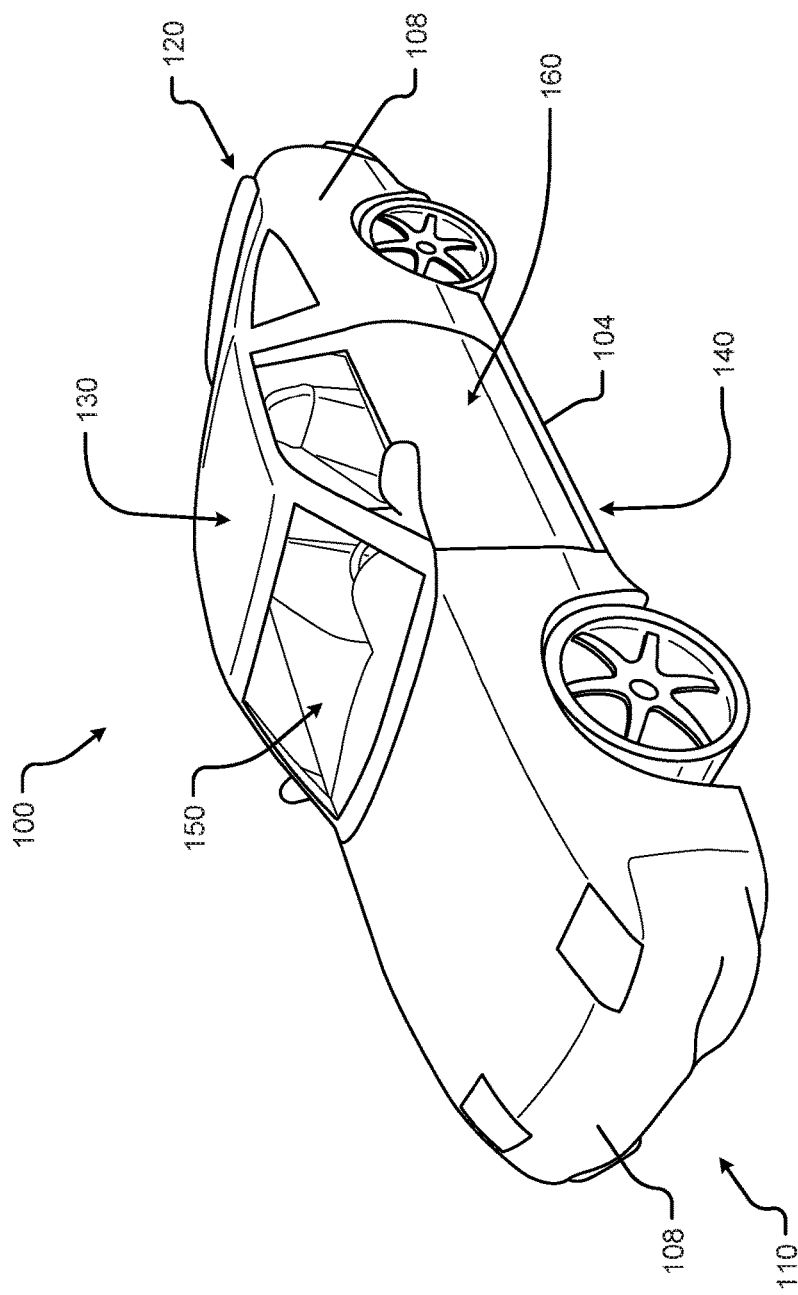
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

Figure 2:
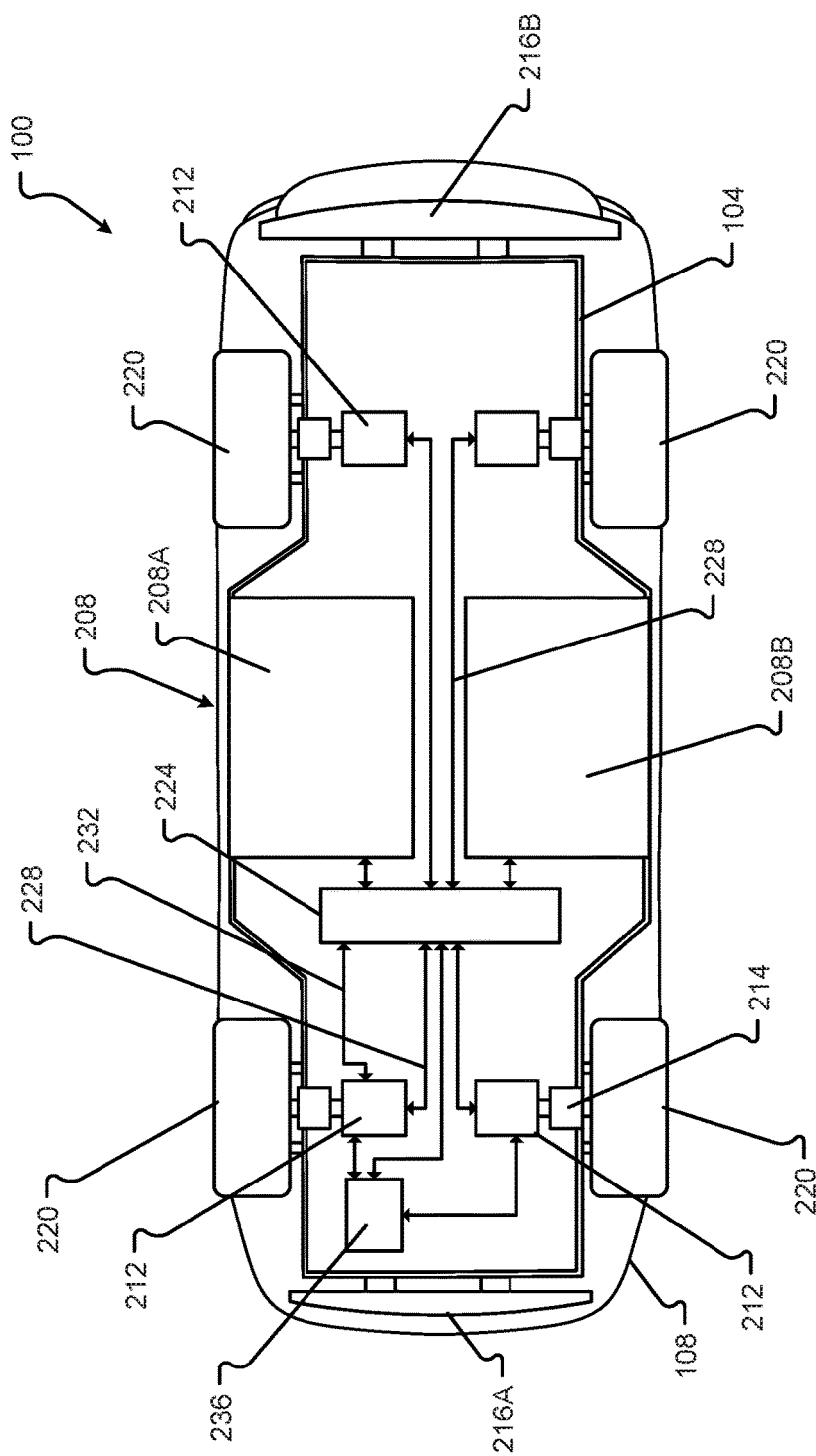
FIG. 2 shows a plan view of the vehicle in accordance with at least some embodiments of the present disclosure.

Referring now to FIG. 2, a plan view of a vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 104 of the vehicle 100. The frame 104 may comprise a separate frame and body construction (i.e., body-on-frame construction), a unitary frame and body construction (i.e., a unibody construction), or any other construction defining the structure of the vehicle 100. The frame 104 may be made from one or more materials including, but in no way limited to steel, titanium, aluminum, carbon fiber, plastic, polymers, etc., and/or combinations thereof. In some embodiments, the frame 104 may be formed, welded, fused, fastened, pressed, etc., combinations thereof, or otherwise shaped to define a physical structure and strength of the vehicle 100. In any event, the frame 104 may comprise one or more surfaces, connections, protrusions, cavities, mounting points, tabs, slots, or other features that are configured to receive other components that make up the vehicle 100. For example, the body panels 108, powertrain subsystem, controls systems, interior components, communications subsystem, and safety subsystem may interconnect with, or attach to, the frame 104 of the vehicle 100.

The frame 104 may include one or more modular system and/or subsystem connection mechanisms. These mechanisms may include features that are configured to provide a selectively interchangeable interface for one or more of the systems and/or subsystems described herein. The mechanisms may provide for a quick exchange, or swapping, of components while providing enhanced security and adaptability over conventional manufacturing or attachment. For instance, the ability to selectively interchange systems and/or subsystems in the vehicle 100 allow the vehicle 100 to adapt to the ever-changing technological demands of society and advances in safety. Among other things, the mechanisms may provide for the quick exchange of batteries, capacitors, power sources 208A, 208B, motors 212, engines, safety equipment, controllers, user interfaces, interiors exterior components, body panels 108, bumpers 216, sensors, etc., and/or combinations thereof. Additionally or alternatively, the mechanisms may provide unique security hardware and/or software embedded therein that, among other things, can prevent fraudulent or low quality construction replacements from being used in the vehicle 100. Similarly, the mechanisms, subsystems, and/or receiving features in the vehicle 100 may employ poka-yoke, or mistake-proofing, features that ensure a particular mechanism is always interconnected with the vehicle 100 in a correct position, function, etc.

By way of example, complete systems or subsystems may be removed and/or replaced from a vehicle 100 utilizing a single-minute exchange ("SME") principle. In some embodiments, the frame 104 may include slides, receptacles, cavities, protrusions, and/or a number of other features that allow for quick exchange of system components. In one embodiment, the frame 104 may include tray or ledge features, mechanical interconnection features, locking mechanisms, retaining mechanisms, etc., and/or combinations thereof. In some embodiments, it may be beneficial to quickly remove a used power source 208A, 208B (e.g., battery unit, capacitor unit, etc.) from the vehicle 100 and replace the used power source 208A, 208B with a charged or new power source. Continuing this example, the power source 208A, 208B may include selectively interchangeable features that interconnect with the frame 104 or other portion of the vehicle 100. For instance, in a power source 208A, 208B replacement, the quick release features may be configured to release the power source 208A, 208B from an engaged position and slide or move in a direction away from the frame 104 of a vehicle 100. Once removed, or separated from, the vehicle, the power source 208A, 208B may be replaced (e.g., with a new power source, a charged power source, etc.) by engaging the replacement power source into a system receiving position adjacent to the vehicle 100. In some embodiments, the vehicle 100 may include one or more actuators configured to position, lift, slide, or otherwise engage the replacement power source with the vehicle 100. In one embodiment, the replacement power source may be inserted into the vehicle 100 or vehicle frame 104 with mechanisms and/or machines that are external and/or separate from the vehicle 100.

In some embodiments, the frame 104 may include one or more features configured to selectively interconnect with other vehicles and/or portions of vehicles. These selectively interconnecting features can allow for one or more vehicles to selectively couple together and decouple for a variety of purposes. For example, it is an aspect of the present disclosure that a number of vehicles may be selectively coupled together to share energy, increase power output, provide security, decrease power consumption, provide towing services, and/or provide a range of other benefits. Continuing this example, the vehicles may be coupled together based on travel route, destination, preferences, settings, sensor information, and/or some other data. The coupling may be initiated by at least one controller of the vehicle and/or traffic control system upon determining that a coupling is beneficial to one or more vehicles in a group of vehicles or a traffic system. As can be appreciated, the power consumption for a group of vehicles traveling in a same direction may be reduced or decreased by removing any aerodynamic separation between vehicles. In this case, the vehicles may be coupled together to subject only the foremost vehicle in the coupling to air and/or wind resistance during travel. In one embodiment, the power output by the group of vehicles may be proportionally or selectively controlled to provide a specific output from each of the one or more of the vehicles in the group.

The interconnecting, or coupling, features may be configured as electromagnetic mechanisms, mechanical couplings, electromechanical coupling mechanisms, etc., and/or combinations thereof. The features may be selectively deployed from a portion of the frame 104 and/or body of the vehicle 100. In some cases, the features may be built into the frame 104 and/or body of the vehicle 100. In any event, the features may deploy from an unexposed position to an exposed position or may be configured to selectively engage/disengage without requiring an exposure or deployment of the mechanism from the frame 104 and/or body of the vehicle 100. In some embodiments, the interconnecting features may be configured to interconnect one or more of power, communications, electrical energy, fuel, and/or the like. One or more of the power, mechanical, and/or communications connections between vehicles may be part of a single interconnection mechanism. In some embodiments, the interconnection mechanism may include multiple connection mechanisms. In any event, the single interconnection mechanism or the interconnection mechanism may employ the poka-yoke features as described above.

The power system of the vehicle 100 may include the powertrain, power distribution system, accessory power system, and/or any other components that store power, provide power, convert power, and/or distribute power to one or more portions of the vehicle 100. The powertrain may include the one or more electric motors 212 of the vehicle 100. The electric motors 212 are configured to convert electrical energy provided by a power source into mechanical energy. This mechanical energy may be in the form of a rotational or other output force that is configured to propel or otherwise provide a motive force for the vehicle 100.

In some embodiments, the vehicle 100 may include one or more drive wheels 220 that are driven by the one or more electric motors 212 and motor controllers 214. In some cases, the vehicle 100 may include an electric motor 212 configured to provide a driving force for each drive wheel 220. In other cases, a single electric motor 212 may be configured to share an output force between two or more drive wheels 220 via one or more power transmission components. It is an aspect of the present disclosure that the powertrain may include one or more power transmission components, motor controllers 214, and/or power controllers that can provide a controlled output of power to one or more of the drive wheels 220 of the vehicle 100. The power transmission components, power controllers, or motor controllers 214 may be controlled by at least one other vehicle controller or computer system as described herein.

As provided above, the powertrain of the vehicle 100 may include one or more power sources 208A, 208B. These one or more power sources 208A, 208B may be configured to provide drive power, system and/or subsystem power, accessory power, etc. While described herein as a single power source 208 for sake of clarity, embodiments of the present disclosure are not so limited. For example, it should be appreciated that independent, different, or separate power sources 208A, 208B may provide power to various systems of the vehicle 100. For instance, a drive power source may be configured to provide the power for the one or more electric motors 212 of the vehicle 100, while a system power source may be configured to provide the power for one or more other systems and/or subsystems of the vehicle 100. Other power sources may include an accessory power source, a backup power source, a critical system power source, and/or other separate power sources. Separating the power sources 208A, 208B in this manner may provide a number of benefits over conventional vehicle systems. For example, separating the power sources 208A, 208B allow one power source 208 to be removed and/or replaced independently without requiring that power be removed from all systems and/or subsystems of the vehicle 100 during a power source 208 removal/replacement. For instance, one or more of the accessories, communications, safety equipment, and/or backup power systems, etc., may be maintained even when a particular power source 208A, 208B is depleted, removed, or becomes otherwise inoperable.

In some embodiments, the drive power source may be separated into two or more cells, units, sources, and/or systems. By way of example, a vehicle 100 may include a first drive power source 208A and a second drive power source 208B. The first drive power source 208A may be operated independently from or in conjunction with the second drive power source 208B and vice versa. Continuing this example, the first drive power source 208A may be removed from a vehicle while a second drive power source 208B can be maintained in the vehicle 100 to provide drive power. This approach allows the vehicle 100 to significantly reduce weight (e.g., of the first drive power source 208A, etc.) and improve power consumption, even if only for a temporary period of time. In some cases, a vehicle 100 running low on power may automatically determine that pulling over to a rest area, emergency lane, and removing, or "dropping off," at least one power source 208A, 208B may reduce enough weight of the vehicle 100 to allow the vehicle 100 to navigate to the closest power source replacement and/or charging area. In some embodiments, the removed, or "dropped off," power source 208A may be collected by a collection service, vehicle mechanic, tow truck, or even another vehicle or individual.

The power source 208 may include a GPS or other geographical location system that may be configured to emit a location signal to one or more receiving entities. For instance, the signal may be broadcast or targeted to a specific receiving party. Additionally or alternatively, the power source 208 may include a unique identifier that may be used to associate the power source 208 with a particular vehicle 100 or vehicle user. This unique identifier may allow an efficient recovery of the power source 208 dropped off. In some embodiments, the unique identifier may provide information for the particular vehicle 100 or vehicle user to be billed or charged with a cost of recovery for the power source 208.

The power source 208 may include a charge controller 224 that may be configured to determine charge levels of the power source 208, control a rate at which charge is drawn from the power source 208, control a rate at which charge is added to the power source 208, and/or monitor a health of the power source 208 (e.g., one or more cells, portions, etc.). In some embodiments, the charge controller 224 or the power source 208 may include a communication interface. The communication interface can allow the charge controller 224 to report a state of the power source 208 to one or more other controllers of the vehicle 100 or even communicate with a communication device separate and/or apart from the vehicle 100. Additionally or alternatively, the communication interface may be configured to receive instructions (e.g., control instructions, charge instructions, communication instructions, etc.) from one or more other controllers or computers of the vehicle 100 or a communication device that is separate and/or apart from the vehicle 100.

The powertrain includes one or more power distribution systems configured to transmit power from the power source 208 to one or more electric motors 212 in the vehicle 100. The power distribution system may include electrical interconnections 228 in the form of cables, wires, traces, wireless power transmission systems, etc., and/or combinations thereof. It is an aspect of the present disclosure that the vehicle 100 include one or more redundant electrical interconnections 232 of the power distribution system. The redundant electrical interconnections 232 can allow power to be distributed to one or more systems and/or subsystems of the vehicle 100 even in the event of a failure of an electrical interconnection portion of the vehicle 100 (e.g., due to an accident, mishap, tampering, or other harm to a particular electrical interconnection, etc.). In some embodiments, a user of a vehicle 100 may be alerted via a user interface associated with the vehicle 100 that a redundant electrical interconnection 232 is being used and/or damage has occurred to a particular area of the vehicle electrical system. In any event, the one or more redundant electrical interconnections 232 may be configured along completely different routes than the electrical interconnections 228 and/or include different modes of failure than the electrical interconnections 228 to, among other things, prevent a total interruption power distribution in the event of a failure.

In some embodiments, the power distribution system may include an energy recovery system 236. This energy recovery system 236, or kinetic energy recovery system, may be configured to recover energy produced by the movement of a vehicle 100. The recovered energy may be stored as electrical and/or mechanical energy. For instance, as a vehicle 100 travels or moves, a certain amount of energy is required to accelerate, maintain a speed, stop, or slow the vehicle 100. In any event, a moving vehicle has a certain amount of kinetic energy. When brakes are applied in a typical moving vehicle, most of the kinetic energy of the vehicle is lost as the generation of heat in the braking mechanism. In an energy recovery system 236, when a vehicle 100 brakes, at least a portion of the kinetic energy is converted into electrical and/or mechanical energy for storage. Mechanical energy may be stored as mechanical movement (e.g., in a flywheel, etc.) and electrical energy may be stored in batteries, capacitors, and/or some other electrical storage system. In some embodiments, electrical energy recovered may be stored in the power source 208. For example, the recovered electrical energy may be used to charge the power source 208 of the vehicle 100.

The vehicle 100 may include one or more safety systems. Vehicle safety systems can include a variety of mechanical and/or electrical components including, but in no way limited to, low impact or energy-absorbing bumpers 216A, 216B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.) or a communication device associated with the vehicle 100 (e.g., across a communication network, etc.).

Figure 3:
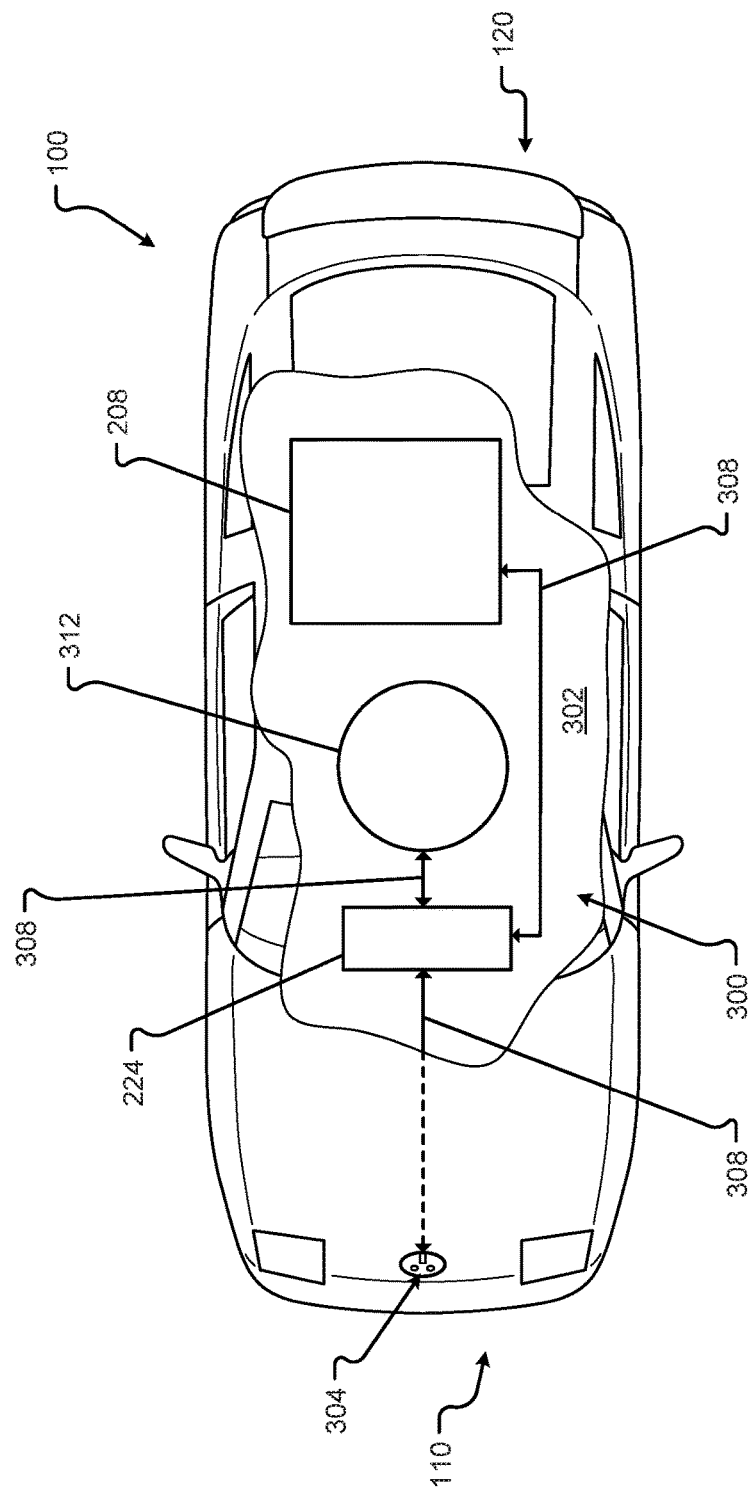
FIG. 3 shows a plan view of the vehicle in accordance with embodiments of the present disclosure

FIG. 3 shows a plan view of the vehicle 100 in accordance with embodiments of the present disclosure. In particular, FIG. 3 shows a broken section 302 of a charging system 300 for the vehicle 100. The charging system 300 may include a plug or receptacle 304 configured to receive power from an external power source (e.g., a source of power that is external to and/or separate from the vehicle 100, etc.). An example of an external power source may include the standard industrial, commercial, or residential power that is provided across power lines. Another example of an external power source may include a proprietary power system configured to provide power to the vehicle 100. In any event, power received at the plug/receptacle 304 may be transferred via at least one power transmission interconnection 308. Similar, if not identical, to the electrical interconnections 228 described above, the at least one power transmission interconnection 308 may be one or more cables, wires, traces, wireless power transmission systems, etc., and/or combinations thereof. Electrical energy in the form of charge can be transferred from the external power source to the charge controller 224. As provided above, the charge controller 224 may regulate the addition of charge to at least one power source 208 of the vehicle 100 (e.g., until the at least one power source 208 is full or at a capacity, etc.).

In some embodiments, the vehicle 100 may include an inductive charging system and inductive charger 312. The inductive charger 312 may be configured to receive electrical energy from an inductive power source external to the vehicle 100. In one embodiment, when the vehicle 100 and/or the inductive charger 312 is positioned over an inductive power source external to the vehicle 100, electrical energy can be transferred from the inductive power source to the vehicle 100. For example, the inductive charger 312 may receive the charge and transfer the charge via at least one power transmission interconnection 308 to the charge controller 324 and/or the power source 208 of the vehicle 100. The inductive charger 312 may be concealed in a portion of the vehicle 100 (e.g., at least partially protected by the frame 104, one or more body panels 108, a shroud, a shield, a protective cover, etc., and/or combinations thereof) and/or may be deployed from the vehicle 100. In some embodiments, the inductive charger 312 may be configured to receive charge only when the inductive charger 312 is deployed from the vehicle 100. In other embodiments, the inductive charger 312 may be configured to receive charge while concealed in the portion of the vehicle 100.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
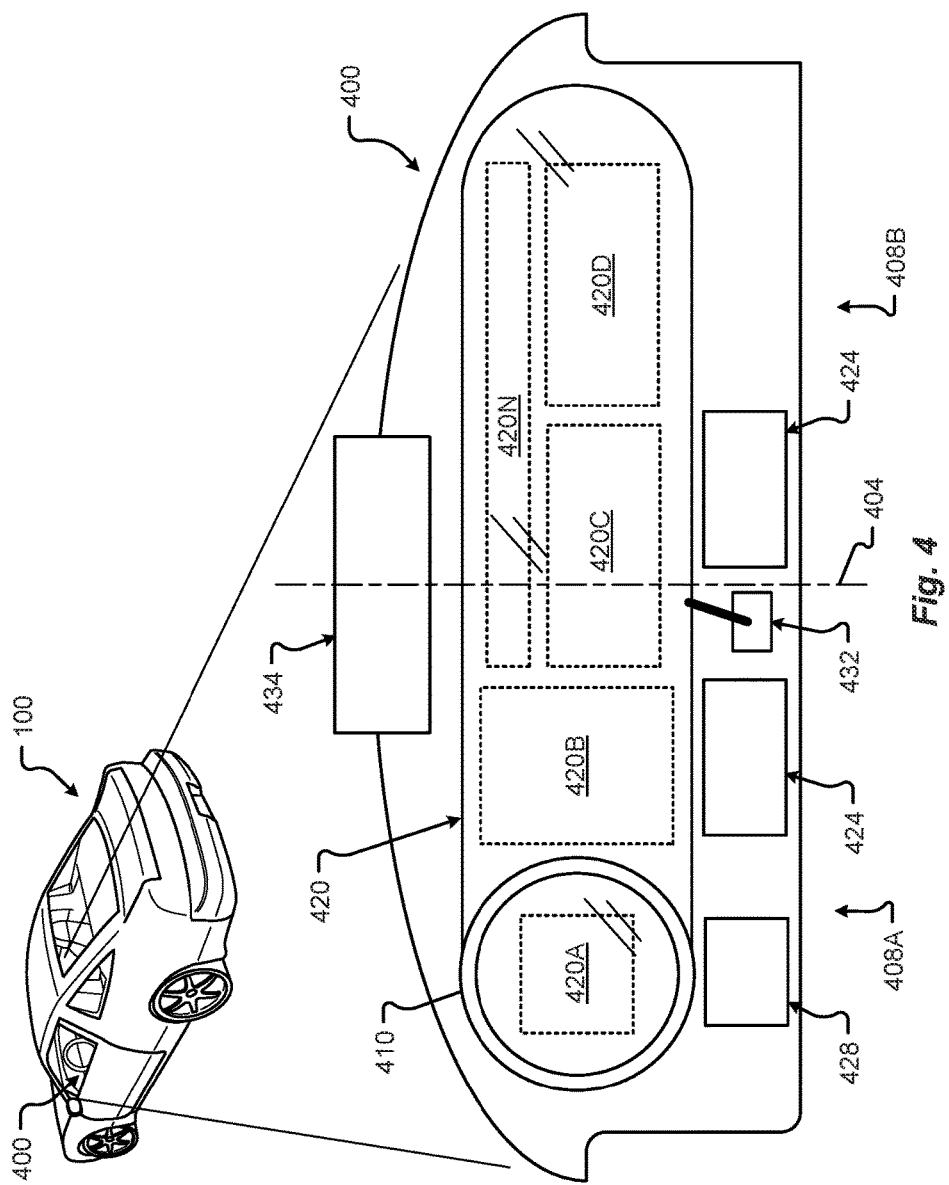
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
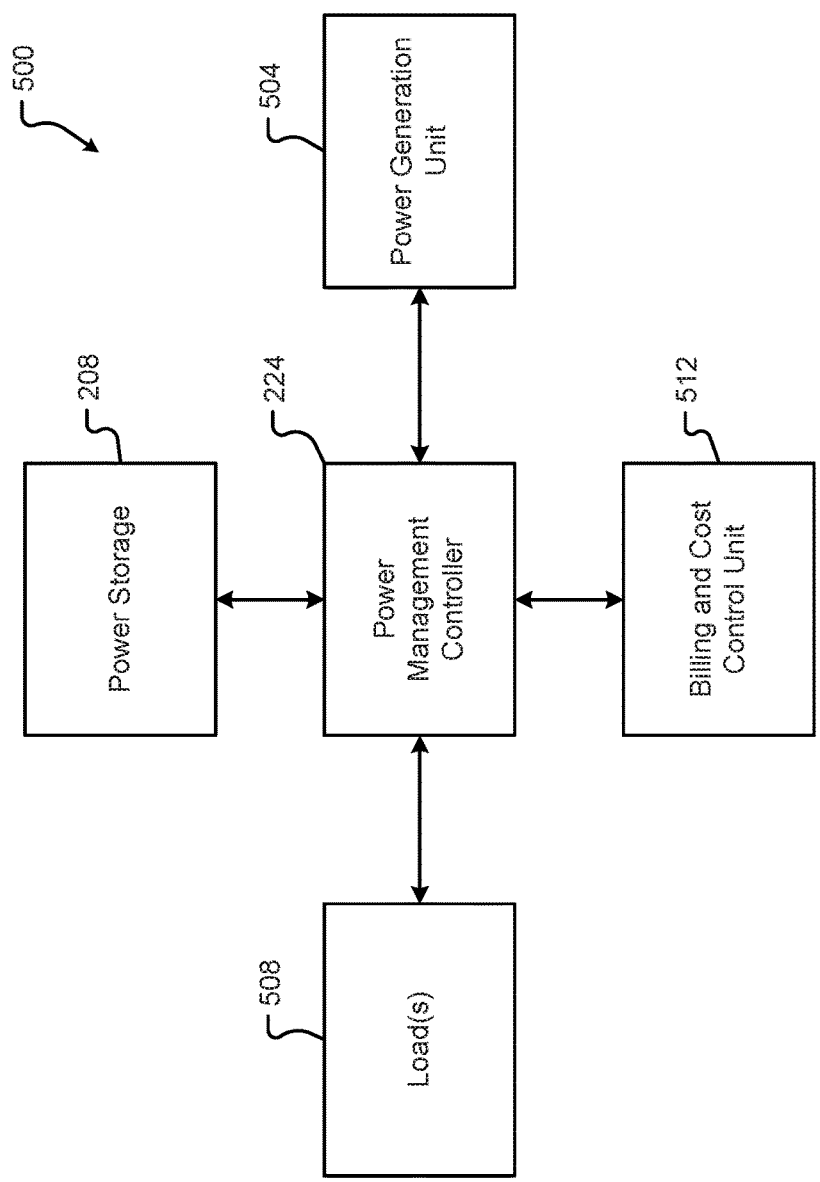
FIG. 5 is a block diagram of an embodiment of an electrical system of the vehicle.

An embodiment of the electrical system 500 associated with the vehicle 100 may be as shown in FIG. 5. The electrical system 500 can include power source(s) that generate power, power storage that stores power, and/or load(s) that consume power. Power sources may be associated with a power generation unit 504. Power storage may be associated with a power storage system 208. Loads may be associated with loads 508. The electrical system 500 may be managed by a power management controller 224. Further, the electrical system 500 can include one or more other interfaces or controllers, which can include the billing and cost control unit 512.

Figure 6:
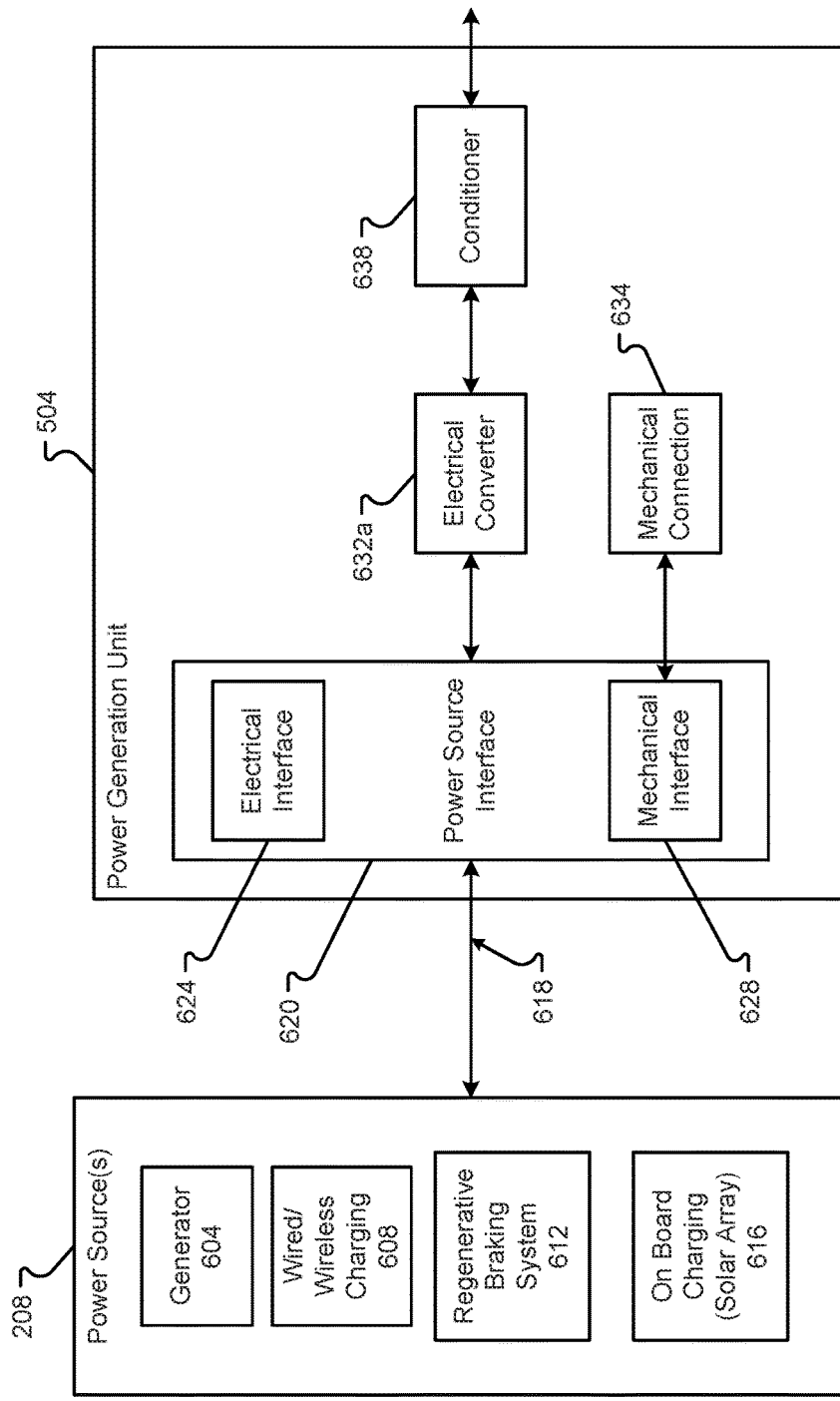
FIG. 6 is a block diagram of an embodiment of a power generation unit associated with the electrical system of the vehicle.

The power generation unit 504 may be as described in conjunction with FIG. 6. The power storage component 208 may be as described in conjunction with FIG. 7. The loads 508 may be as described in conjunction with FIG. 8.

The billing and cost control unit 512 may interface with the power management controller 224 to determine the amount of charge or power provided to the power storage 208 through the power generation unit 504. The billing and cost control unit 512 can then provide information for billing the vehicle owner. Thus, the billing and cost control unit 512 can receive and/or send power information to third party system(s) regarding the received charge from an external source. The information provided can help determine an amount of money required, from the owner of the vehicle, as payment for the provided power. Alternatively, or in addition, if the owner of the vehicle provided power to another vehicle (or another device/system), that owner may be owed compensation for the provided power or energy, e.g., a credit.

The power management controller 224 can be a computer or computing system(s) and/or electrical system with associated components, as described herein, capable of managing the power generation unit 504 to receive power, routing the power to the power storage 208, and then providing the power from either the power generation unit 504 and/or the power storage 208 to the loads 508. Thus, the power management controller 224 may execute programming that controls switches, devices, components, etc. involved in the reception, storage, and provision of the power in the electrical system 500.

An embodiment of the power generation unit 504 may be as shown in FIG. 6. Generally, the power generation unit 504 may be electrically coupled to one or more power sources 208. The power sources 208 can include power sources internal and/or associated with the vehicle 100 and/or power sources external to the vehicle 100 to which the vehicle 100 electrically connects. One of the internal power sources can include an on board generator 604. The generator 604 may be an alternating current (AC) generator, a direct current (DC) generator or a self-excited generator. The AC generators can include induction generators, linear electric generators, and/or other types of generators. The DC generators can include homopolar generators and/or other types of generators. The generator 604 can be brushless or include brush contacts and generate the electric field with permanent magnets or through induction. The generator 604 may be mechanically coupled to a source of kinetic energy, such as an axle or some other power take-off. The generator 604 may also have another mechanical coupling to an exterior source of kinetic energy, for example, a wind turbine.

Another power source 208 may include wired or wireless charging 608. The wireless charging system 608 may include inductive and/or resonant frequency inductive charging systems that can include coils, frequency generators, controllers, etc. Wired charging may be any kind of grid-connected charging that has a physical connection, although, the wireless charging may be grid connected through a wireless interface. The wired charging system can include connectors, wired interconnections, the controllers, etc. The wired and wireless charging systems 608 can provide power to the power generation unit 504 from external power sources 208.

Internal sources for power may include a regenerative braking system 612. The regenerative braking system 612 can convert the kinetic energy of the moving car into electrical energy through a generation system mounted within the wheels, axle, and/or braking system of the vehicle 100. The regenerative braking system 612 can include any coils, magnets, electrical interconnections, converters, controllers, etc. required to convert the kinetic energy into electrical energy.

Another source of power 208, internal to or associated with the vehicle 100, may be a solar array 616. The solar array 616 may include any system or device of one or more solar cells mounted on the exterior of the vehicle 100 or integrated within the body panels of the vehicle 100 that provides or converts solar energy into electrical energy to provide to the power generation unit 504.

The power sources 208 may be connected to the power generation unit 504 through an electrical interconnection 618. The electrical interconnection 618 can include any wire, interface, bus, etc. between the one or more power sources 208 and the power generation unit 504.

The power generation unit 504 can also include a power source interface 620. The power source interface 620 can be any type of physical and/or electrical interface used to receive the electrical energy from the one or more power sources 208; thus, the power source interface 620 can include an electrical interface 624 that receives the electrical energy and a mechanical interface 628 which may include wires, connectors, or other types of devices or physical connections. The mechanical interface 608 can also include a physical/electrical connection 634 to the power generation unit 504.

The electrical energy from the power source 208 can be processed through the power source interface 624 to an electric converter 632. The electric converter 632 may convert the characteristics of the power from one of the power sources into a useable form that may be used either by the power storage 208 or one or more loads 508 within the vehicle 100. The electrical converter 624 may include any electronics or electrical devices and/or component that can change electrical characteristics, e.g., AC frequency, amplitude, phase, etc. associated with the electrical energy provided by the power source 208. The converted electrical energy may then be provided to an optional conditioner 1638. The conditioner 1638 may include any electronics or electrical devices and/or component that may further condition the converted electrical energy by removing harmonics, noise, etc. from the electrical energy to provide a more stable and effective form of power to the vehicle 100.

Figure 7:
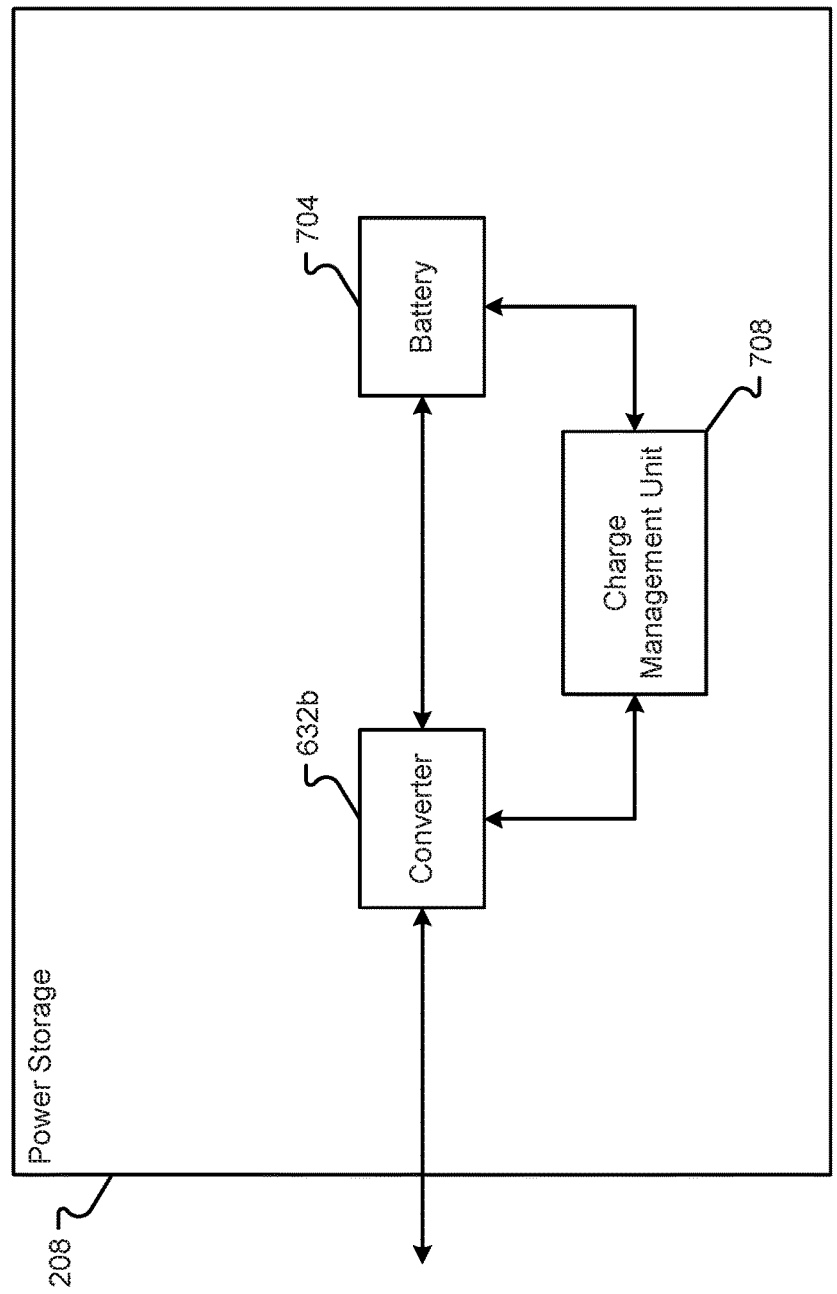
FIG. 7 is a block diagram of an embodiment of power storage associated with the electrical system of the vehicle.

An embodiment of the power storage 208 may be as shown in FIG. 7. The power storage unit can include an electrical converter 632*b*, one or more batteries, one or more rechargeable batteries, one or more capacitors, one or more accumulators, one or more supercapacitors, one or more ultrabatteries, and/or superconducting magnetics 704, and/or a charge management unit 708. The converter 632*b* may be the same or similar to the electrical converter 632*a* shown in FIG. 6. The converter 632*b* may be a replacement for the electric converter 632*a* shown in FIG. 6 and thus eliminate the need for the electrical converter 632*a* as shown in FIG. 6. However, if the electrical converter 632*a* is provided in the power generation unit 504, the converter 632*b*, as shown in the power storage unit 208, may be eliminated. The converter 632*b* can also be redundant or different from the electrical converter 632*a* shown in FIG. 6 and may provide a different form of energy to the battery and/or capacitors 704. Thus, the converter 632*b* can change the energy characteristics specifically for the battery/capacitor 704.

The battery 704 can be any type of battery for storing electrical energy, for example, a lithium ion battery, a lead acid battery, a nickel cadmium battery, etc. Further, the battery 704 may include different types of power storage systems, such as, ionic fluids or other types of fuel cell systems. The energy storage 704 may also include one or more high-capacity capacitors 704. The capacitors 704 may be used for long-term or short-term storage of electrical energy. The input into the battery or capacitor 704 may be different from the output, and thus, the capacitor 704 may be charged quickly but drain slowly. The functioning of the converter 632 and battery capacitor 704 may be monitored or managed by a charge management unit 708.

The charge management unit 708 can include any hardware (e.g., any electronics or electrical devices and/or components), software, or firmware operable to adjust the operations of the converter 632 or batteries/capacitors 704. The charge management unit 708 can receive inputs or periodically monitor the converter 632 and/or battery/capacitor 704 from this information; the charge management unit 708 may then adjust settings or inputs into the converter 632 or battery/capacitor 704 to control the operation of the power storage system 208.

Figure 8:
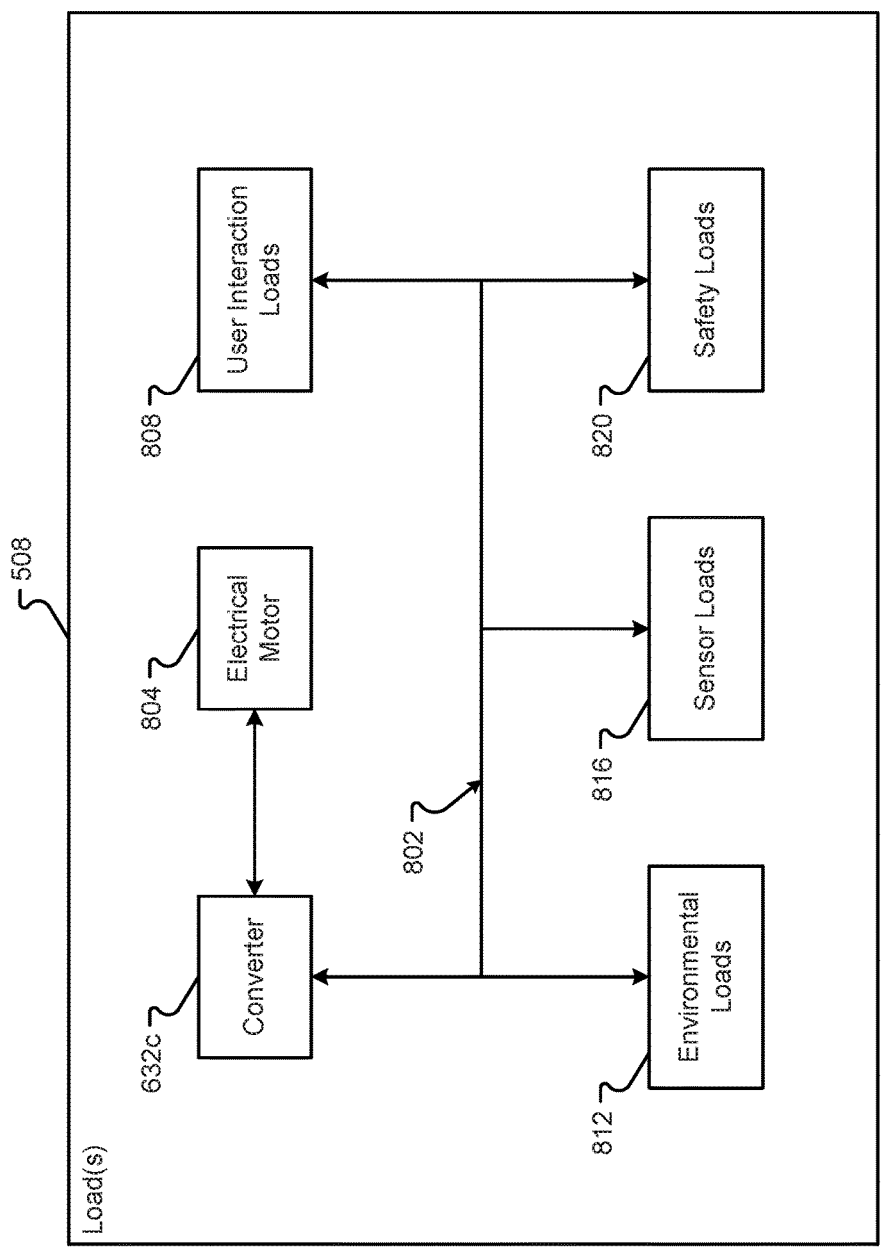
FIG. 8 is a block diagram of an embodiment of loads associated with the electrical system of the vehicle.

An embodiment of one or more loads 508 associated with the vehicle 100 may be as shown in FIG. 8. The loads 508 may include a bus or electrical interconnection system 802, which provides electrical energy to one or more different loads within the vehicle 100. The bus 802 can be any number of wires or interfaces used to connect the power generation unit 504 and/or power storage 208 to the one or more loads 508. The converter 632*c* may be an interface from the power generation unit 504 or the power storage 208 into the loads 508. The converter 632*c* may be the same or similar to electric converter 632*a* as shown in FIG. 6. Similar to the discussion of the converter 632*b* in FIG. 7, the converter 632*c* may be eliminated, if the electric converter 632*a*, shown in FIG. 6, is present. However, the converter 632*c* may further condition or change the energy characteristics for the bus 802 for use by the loads 508. The converter 632*c* may also provide electrical energy to electric motor 804, which may power the vehicle 100.

The electric motor 804 can be any type of DC or AC electric motor. The electric motor may be a direct drive or induction motor using permanent magnets and/or winding either on the stator or rotor. The electric motor 804 may also be wireless or include brush contacts. The electric motor 804 may be capable of providing a torque and enough kinetic energy to move the vehicle 100 in traffic. In some embodiments, the electric motor 804 may be similar, if not identical, to the electric motor 212 described in conjunction with FIG. 2.

The different loads 508 may also include environmental loads 812, sensor loads 816, safety loads 820, user interaction loads 808, etc. User interaction loads 808 can be any energy used by user interfaces or systems that interact with the driver and/or passenger(s) of the vehicle 100. These loads 808 may include, for example, the heads up display 434, the dash display 420, 424, 428, the radio, user interfaces on the head unit, lights, radio, and/or other types of loads that provide or receive information from the occupants of the vehicle 100. The environmental loads 812 can be any loads used to control the environment within the vehicle 100. For example, the air conditioning or heating unit of the vehicle 100 can be environmental loads 812. Other environmental loads can include lights, fans, and/or defrosting units, etc. that may control the environment within, and/or outside of, the vehicle 100. The sensor loads 816 can be any loads used by sensors, for example, air bag sensors, GPS, and other such sensors used to either manage or control the vehicle 100 and/or provide information or feedback to the vehicle occupants. The safety loads 820 can include any safety equipment, for example, seat belt alarms, airbags, headlights, blinkers, etc. that may be used to manage the safety of the occupants of the vehicle 100. There may be more or fewer loads than those described herein, although they may not be shown in FIG. 8.

Figure 9:
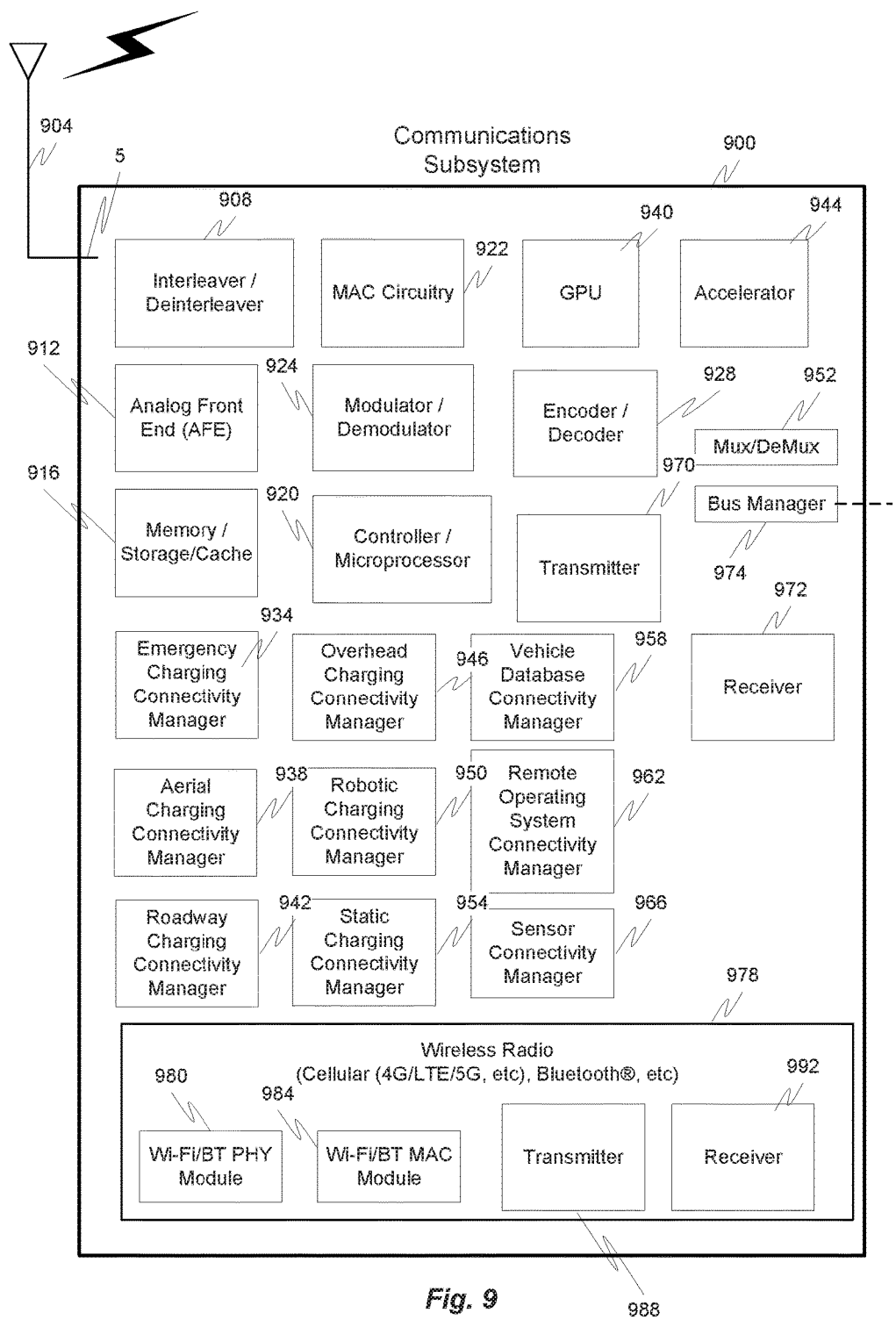
FIG. 9 is a block diagram of an embodiment of a communications subsystem of the vehicle.

FIG. 9 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem can include one or more communications links (that can be wired or wireless) and/or communications busses (managed by the bus manager 974), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem enables communications between any if the inter-vehicle systems and subsystems as well as communications with non-collocated resources, such as those reachable over a network such as the Internet.

The communications subsystem 900, in addition to well-known componentry (which has been omitted for clarity), includes interconnected elements including one or more of: one or more antennas 904, an interleaver/deinterleaver 908, an analog front end (AFE) 912, memory/storage/cache 916, controller/microprocessor 920, MAC circuitry 922, modulator/demodulator 924, encoder/decoder 928, a plurality of connectivity managers 934-966, GPU 940, accelerator 944, a multiplexer/demultiplexer 952, transmitter 970, receiver 972 and wireless radio 978 components such as a Wi-Fi PHY/Bluetooth® module 980, a Wi-Fi/BT MAC module 984, transmitter 988 and receiver 992. The various elements in the device 900 are connected by one or more links/busses 5 (not shown, again for sake of clarity).

The device 400 can have one more antennas 904, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 904 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 904 generally interact with the Analog Front End (AFE) 912, which is needed to enable the correct processing of the received modulated signal and signal conditioning for a transmitted signal. The AFE 912 can be functionally located between the antenna and a digital baseband system in order to convert the analog signal into a digital signal for processing and vice-versa.

The subsystem 900 can also include a controller/microprocessor 920 and a memory/storage/cache 916. The subsystem 900 can interact with the memory/storage/cache 916 which may store information and operations necessary for configuring and transmitting or receiving the information described herein. The memory/storage/cache 916 may also be used in connection with the execution of application programming or instructions by the controller/microprocessor 920, and for temporary or long term storage of program instructions and/or data. As examples, the memory/storage/cache 920 may comprise a computer-readable device, RAM, ROM, DRAM, SDRAM, and/or other storage device(s) and media.

The controller/microprocessor 920 may comprise a general purpose programmable processor or controller for executing application programming or instructions related to the subsystem 900. Furthermore, the controller/microprocessor 920 can perform operations for configuring and transmitting/receiving information as described herein. The controller/microprocessor 920 may include multiple processor cores, and/or implement multiple virtual processors. Optionally, the controller/microprocessor 920 may include multiple physical processors. By way of example, the controller/microprocessor 920 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 900 can further include a transmitter 970 and receiver 972 which can transmit and receive signals, respectively, to and from other devices, subsystems and/or other destinations using the one or more antennas 904 and/or links/busses. Included in the subsystem 900 circuitry is the medium access control or MAC Circuitry 922. MAC circuitry 922 provides for controlling access to the wireless medium. In an exemplary embodiment, the MAC circuitry 922 may be arranged to contend for the wireless medium and configure frames or packets for communicating over the wired/wireless medium.

The subsystem 900 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 900 also includes a GPU 940, an accelerator 944, a Wi-Fi/BT/BLE PHY module 980 and a Wi-Fi/BT/BLE MAC module 984 and wireless transmitter 988 and receiver 992. In some embodiments, the GPU 940 may be a graphics processing unit, or visual processing unit, comprising at least one circuit and/or chip that manipulates and changes memory to accelerate the creation of images in a frame buffer for output to at least one display device. The GPU 940 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 934-966 (even) manage and/or coordinate communications between the subsystem 900 and one or more of the systems disclosed herein and one or more other devices/systems. The connectivity managers include an emergency charging connectivity manager 934, an aerial charging connectivity manager 938, a roadway charging connectivity manager 942, an overhead charging connectivity manager 946, a robotic charging connectivity manager 950, a static charging connectivity manager 954, a vehicle database connectivity manager 958, a remote operating system connectivity manager 962 and a sensor connectivity manager 966.

The emergency charging connectivity manager 934 can coordinate not only the physical connectivity between the vehicle 100 and the emergency charging device/vehicle, but can also communicate with one or more of the power management controller, one or more third parties and optionally a billing system(s). As an example, the vehicle 100 can establish communications with the emergency charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the emergency charging connectivity manager 934 can also communicate information, such as billing information to the emergency charging vehicle and/or a third party. This billing information could be, for example, the owner of the vehicle 100, the driver/occupant(s) of the vehicle 100, company information, or in general any information usable to charge the appropriate entity for the power received.

The aerial charging connectivity manager 938 can coordinate not only the physical connectivity between the vehicle 100 and the aerial charging device/vehicle, but can also communicate with one or more of the power management controller, one or more third parties and optionally a billing system(s). As an example, the vehicle 100 can establish communications with the aerial charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the aerial charging connectivity manager 938 can similarly communicate information, such as billing information to the aerial charging vehicle and/or a third party. This billing information could be, for example, the owner of the vehicle 100, the driver/occupant(s) of the vehicle 100, company information, or in general any information usable to charge the appropriate entity for the power received etc., as discussed.

The roadway charging connectivity manager 942 and overhead charging connectivity manager 946 can coordinate not only the physical connectivity between the vehicle 100 and the charging device/system, but can also communicate with one or more of the power management controller, one or more third parties and optionally a billing system(s). As one example, the vehicle 100 can request a charge from the charging system when, for example, the vehicle 100 needs or is predicted to need power. As an example, the vehicle 100 can establish communications with the charging device/vehicle to one or more of coordinate interconnectivity between the two for charging and share information for billing. Once charging is complete, the amount of charge provided can be tracked and optionally forwarded to, for example, a third party for billing. This billing information could be, for example, the owner of the vehicle 100, the driver/occupant(s) of the vehicle 100, company information, or in general any information usable to charge the appropriate entity for the power received etc., as discussed. The person responsible for paying for the charge could also receive a copy of the billing information as is customary. The robotic charging connectivity manager 950 and static charging connectivity manager 954 can operate in a similar manner to that described herein.

The vehicle database connectivity manager 958 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general any information stored in the vehicle database can optionally be shared with any one or more other devices optionally subject to any privacy or confidentially restrictions.

The remote operating system connectivity manager 962 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 966 facilitates communications between any one or more of the vehicle sensors and any one or more of the other vehicle systems. The sensor connectivity manager 966 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 10:
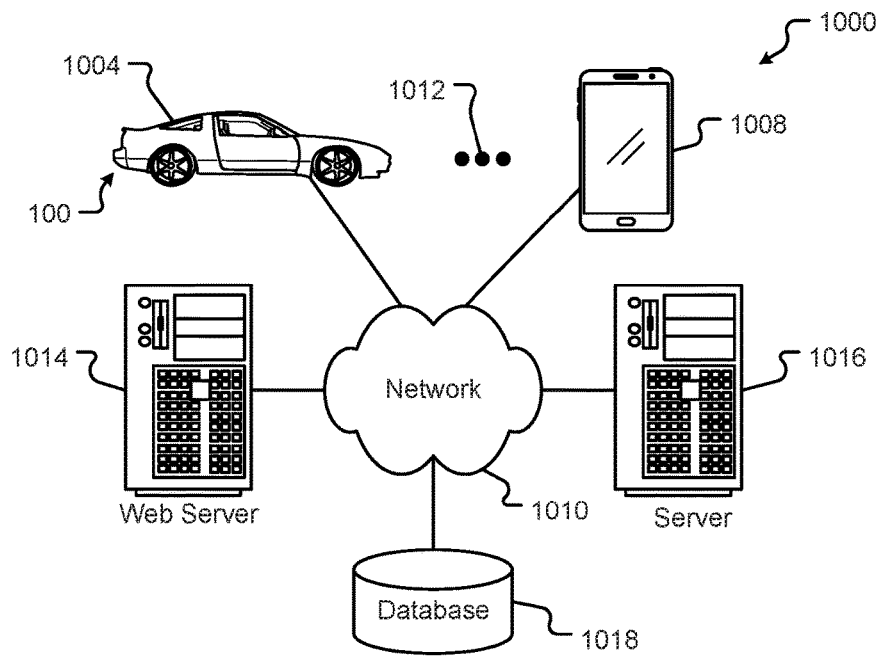
FIG. 10 is a block diagram of a computing environment associated with the embodiments presented herein.

FIG. 10 illustrates a block diagram of a computing environment 1000 that may function as the servers, user computers, or other systems provided and described herein. The environment 1000 includes one or more user computers, or computing devices, such as a vehicle computing device 1004, a communication device 1008, and/or more 1012. The computing devices 1004, 1008, 1012 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 1004, 1008, 1012 may also have any of a variety of applications, including for example, database client and/or server applications, and web browser applications. Alternatively, the computing devices 1004, 1008, 1012 may be any other electronic device, such as a thin-client computer, Internet-enabled mobile telephone, and/or personal digital assistant, capable of communicating via a network 1010 and/or displaying and navigating web pages or other types of electronic documents. Although the exemplary computer environment 1000 is shown with two computing devices, any number of user computers or computing devices may be supported.

Environment 1000 further includes a network 1010. The network 1010 may can be any type of network familiar to those skilled in the art that can support data communications using any of a variety of commercially-available protocols, including without limitation SIP, TCP/IP, SNA, IPX, AppleTalk, and the like. Merely by way of example, the network 1010 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 1014, 1016. In this example, server 1014 is shown as a web server and server 1016 is shown as an application server. The web server 1014, which may be used to process requests for web pages or other electronic documents from computing devices 1004, 1008, 1012. The web server 1014 can be running an operating system including any of those discussed above, as well as any commercially-available server operating systems. The web server 1014 can also run a variety of server applications, including SIP (Session Initiation Protocol) servers, HTTP(s) servers, FTP servers, CGI servers, database servers, Java servers, and the like. In some instances, the web server 1014 may publish operations available operations as one or more web services.

The environment 1000 may also include one or more file and or/application servers 1016, which can, in addition to an operating system, include one or more applications accessible by a client running on one or more of the computing devices 1004, 1008, 1012. The server(s) 1016 and/or 1014 may be one or more general purpose computers capable of executing programs or scripts in response to the computing devices 1004, 1008, 1012. As one example, the server 1016, 1014 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 1016 may also include database servers, including without limitation those commercially available from Oracle®, Microsoft®, Sybase®, IBM® and the like, which can process requests from database clients running on a computing device 1004, 1008, 1012.

The web pages created by the server 1014 and/or 1016 may be forwarded to a computing device 1004, 1008, 1012 via a web (file) server 1014, 1016. Similarly, the web server 1014 may be able to receive web page requests, web services invocations, and/or input data from a computing device 1004, 1008, 1012 (e.g., a user computer, etc.) and can forward the web page requests and/or input data to the web (application) server 1016. In further embodiments, the server 1016 may function as a file server. Although for ease of description, FIG. 10 illustrates a separate web server 1014 and file/application server 1016, those skilled in the art will recognize that the functions described with respect to servers 1014, 1016 may be performed by a single server and/or a plurality of specialized servers, depending on implementation-specific needs and parameters. The computer systems 1004, 1008, 1012, web (file) server 1014 and/or web (application) server 1016 may function as the system, devices, or components described in FIGS. 1-10.

The environment 1000 may also include a database 1018. The database 1018 may reside in a variety of locations. By way of example, database 1018 may reside on a storage medium local to (and/or resident in) one or more of the computers 1004, 1008, 1012, 1014, 1016. Alternatively, it may be remote from any or all of the computers 1004, 1008, 1012, 1014, 1016, and in communication (e.g., via the network 1010) with one or more of these. The database 1018 may reside in a storage-area network ("SAN") familiar to those skilled in the art. Similarly, any necessary files for performing the functions attributed to the computers 1004, 1008, 1012, 1014, 1016 may be stored locally on the respective computer and/or remotely, as appropriate. The database 1018 may be a relational database, such as Oracle 20i®, that is adapted to store, update, and retrieve data in response to SQL-formatted commands.

Figure 11:
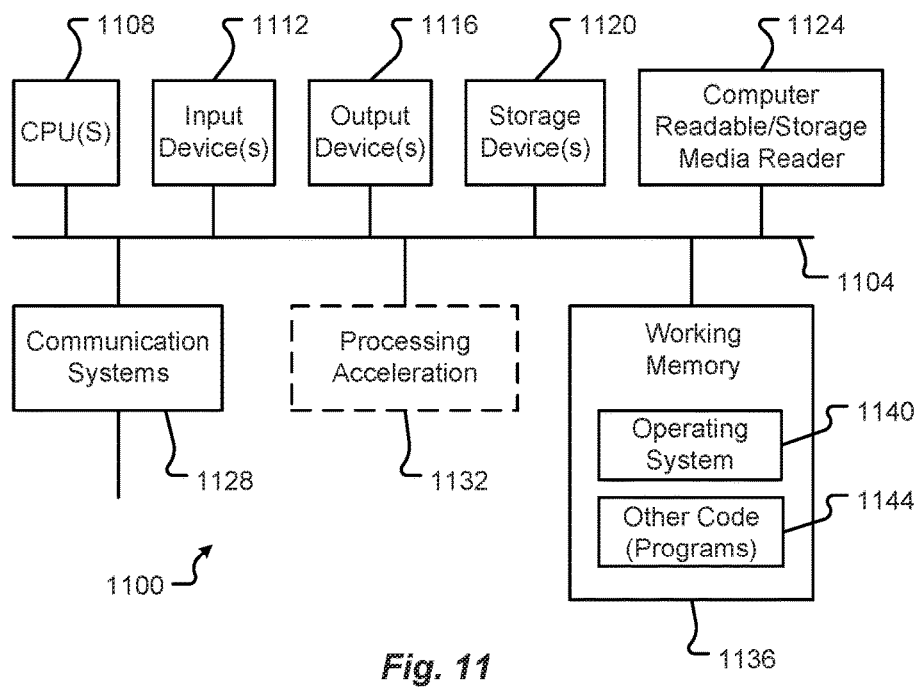
FIG. 11 is a block diagram of a computing device associated with one or more components described herein.

FIG. 11 illustrates one embodiment of a computer system 1100 upon which the servers, user computers, computing devices, or other systems or components described above may be deployed or executed. The computer system 1100 is shown comprising hardware elements that may be electrically coupled via a bus 1104. The hardware elements may include one or more central processing units (CPUs) 1108; one or more input devices 1112 (e.g., a mouse, a keyboard, etc.); and one or more output devices 1116 (e.g., a display device, a printer, etc.). The computer system 1100 may also include one or more storage devices 1120. By way of example, storage device(s) 1120 may be disk drives, optical storage devices, solid-state storage devices such as a random access memory ("RAM") and/or a read-only memory ("ROM"), which can be programmable, flash-updateable and/or the like.

The computer system 1100 may additionally include a computer-readable storage media reader 1124; a communications system 1128 (e.g., a modem, a network card (wireless or wired), an infra-red communication device, etc.); and working memory 1136, which may include RAM and ROM devices as described above. The computer system 1100 may also include a processing acceleration unit 1132, which can include a DSP, a special-purpose processor, and/or the like.

The computer-readable storage media reader 1124 can further be connected to a computer-readable storage medium, together (and, optionally, in combination with storage device(s) 1120) comprehensively representing remote, local, fixed, and/or removable storage devices plus storage media for temporarily and/or more permanently containing computer-readable information. The communications system 1128 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 1100 may also comprise software elements, shown as being currently located within a working memory 1136, including an operating system 1140 and/or other code 1144. It should be appreciated that alternate embodiments of a computer system 1100 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 1108 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 12:
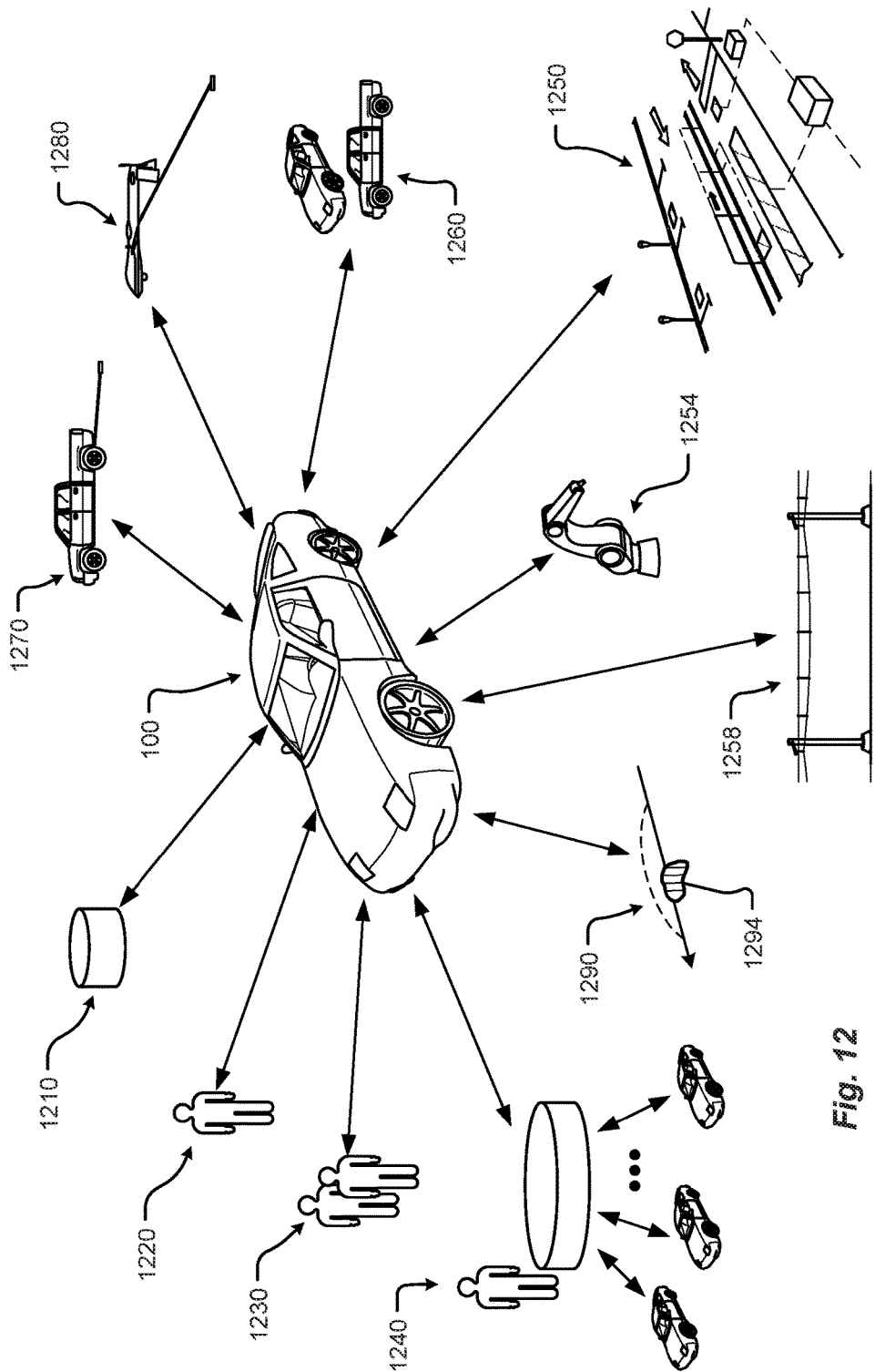
FIG. 12 shows a vehicle in an environment in accordance with embodiments of the present disclosure.

Referring to FIG. 12, the vehicle 100 is shown in a plurality of operational and/or charging environments. The vehicle 100 may operate in any one or more of the depicted environments in any combination. Other embodiments are possible but may not be depicted in FIG. 12. Generally, the vehicle 100 may operate in environments which enable charging of the vehicle 100 and/or operation of the vehicle 100. More specifically, the vehicle 100 may receive a charge via one or more means comprising emergency charging vehicle system 1270, aerial vehicle charging system 1280, roadway system 1250, robotic charging system 1254, and/or overhead charging system 1258. The vehicle 100 may interact and/or operate in an environment comprising one or more other roadway vehicles 1260. The vehicle 100 may engage with elements within the vehicle 100 comprising vehicle driver 1220, vehicle passengers 1230, and/or a vehicle database 1210. In one embodiment, vehicle database 1210 may not physically reside in the vehicle 100 and may instead be accessed remotely (e.g., by wireless communication, etc.), and as such, may reside in another location such as a residence or business location. The vehicle 100 may operate autonomously and/or semi-autonomously in an autonomous environment 1290 (here, depicted as a roadway environment presenting a roadway obstacle 1294 of which the vehicle 100 autonomously identifies and steers the vehicle 100 clear of the obstacle 1294). Furthermore, the vehicle 100 may engage with a remote operator system 1240, which may provide fleet management instructions or control.

In some embodiments, the vehicle 100 may be configured to receive charge via one or more compatible vehicle charging interfaces, such as one or more charging panels and/or interconnections. These compatible vehicle charging interfaces may be configured at one or more locations on, in, or about a vehicle 100. For instance, the locations may include locations on the vehicle 100 wherein charging may be received, via a vehicle roof 130, vehicle side 160 and vehicle lower or undercarriage 140.

In general, A provider or seller of a particular service offered to a user can set rules defining management and/or delivery of those services. The provider may be a repair facility, power charging station or facility, a power source exchange station or facility, or fleet manager and the user may be a vehicle owner or operator. For example, a set of rules can be used to manage services related to use of a battery exchange facility for electric or hybrid vehicles. According to one embodiment, instead of a battery centric model for managing power for the vehicle, a battery agnostic model can be used which can allow users to pay on an amp-hour or other basis. This paradigm could be used in conjunction with the licensing of the battery or multiple batteries, except, instead of licensing the battery or batteries, a service provider or licensor can provide whatever battery or batteries are necessary to meet the purchased power demands. For example, in a fleet environment, a service provider or licensor can provide however many batteries are necessary to supply the fleet with sufficient power to operate their vehicles for a total number of miles per year or other period of time.

Figure 13:
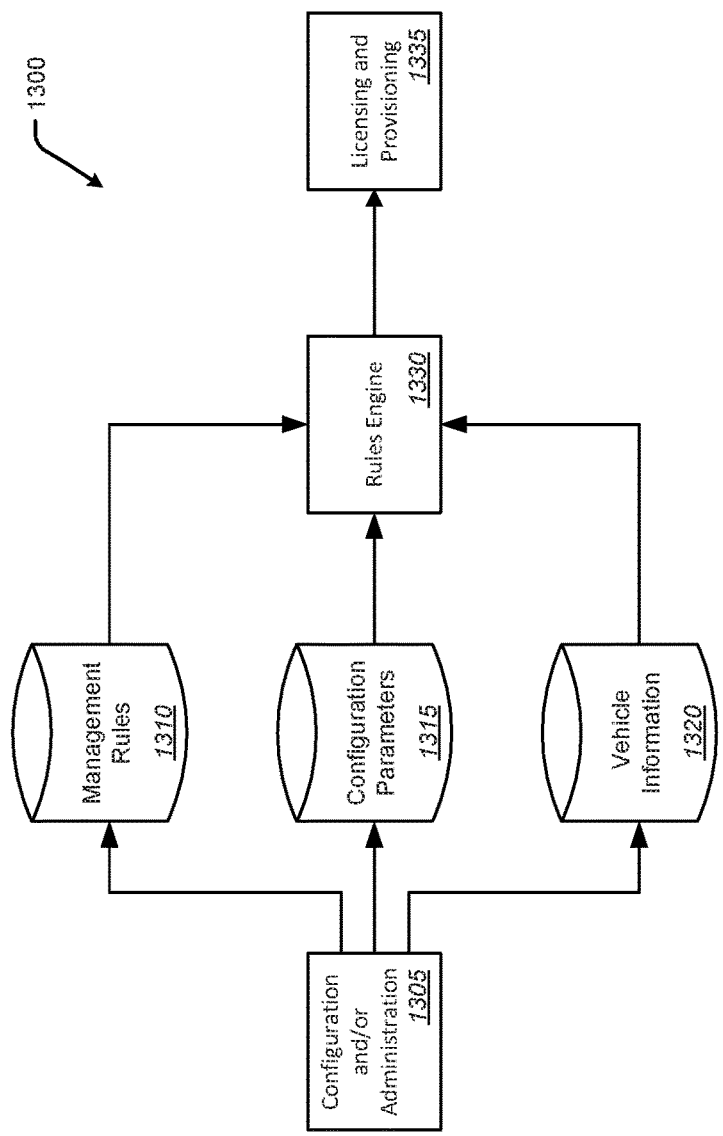
FIG. 13 is a block diagram illustrating components of a system for applying management rules to manage provisioning an amount of power for one or more vehicles according to one embodiment of the present disclosure.

FIG. 13 is a block diagram illustrating components of a system for applying management rules to manage provisioning an amount of power for one or more vehicles according to one embodiment of the present disclosure. As illustrated in this example, a service provider's system 1300 can comprise a configuration and/or administration component 1305, one or more repositories of rules and information including but not limited to a repository of management rules 1310, a repository of configuration parameters 1315, and a repository of vehicle information 1320. The service provider's system 1300 can further comprise a data collection component 1325, a rules engine 1330, and a licensing and/or provisioning component.

Generally speaking, a service provider can, for example using a graphical or other user interface provided by the configuration and/or administration component 1305, define a set of rules saved in the repository of management rules 1310 and/or a set of configuration parameters saved in the repository of configuration parameters 1315. In some cases, the service provider may also be able, through the configuration and/or administration component 1305, define, modify, or view a set of vehicle information saved in the repository of vehicle information 1320. The rules engine 1330 can apply the rules of the repository of maintenance management rules 1310 using the set of configuration parameters saved in the repository of configuration parameters 1315 and the vehicle information saved in the repository of vehicle information 1320 to determine or generate instructions and/or information related to a service available from the service provider to the vehicle such as the licensing of batteries or other power sources to the user of the vehicle. These instructions indicating, for example, type of power source, number of power sources, terms of the license, etc. can be provided to a licensing and/or provisioning component that can then manage the process of providing the determined power sources to the vehicle. Additionally or alternatively, the information can be sent by the licensing and/or provisioning component 1335 to the vehicle or other system, for example, via a cellular or other wireless connection.

More specifically, the service provider or seller of a particular service, such as a battery licensing service, can set rules for managing the services provided by configuring, through the configuration and/or administration component 1305, business rules defining how those services will be delivered. The set of rules can be implemented in any common rule definition language such as, for example, Business Process Execution Language (BPEL) or similar language, and can comprise a set of conditions and associated actions to be applied upon satisfaction of those conditions. The actions can, in some cases, be calculations or other operations to determine a type and/or number of power sources for a requested amount of power for one or more vehicles, a cost for the power sources, etc. Any number and variety of other rules can be implemented at the service provider's discretion and are considered to be within the scope of the present disclosure.

The service provider can, for example, through the graphical or other user interface of the configuration and/or administration component 1305, define and/or adjust selectable or configurable parameters stored in the repository of configuration parameters 1315 to be used by the management rules in order to determine logistics for a requested service. These parameters can comprise, for example, values for variables defined in the calculations or actions of the rules. In other cases, the parameters can comprise switches, flags, or other values for the conditions of the rules. The terms or parameters stored in the repository of configuration parameters 1315 may be varied by the service provider through the configuration and/or administration component 1305 to define terms of the licensing agreement and influence determinations of power source types, numbers, costs, etc. Additionally or alternatively, these parameters can be used to set variables related to capacity and/or performance of particular types of power sources to influence calculations of how many and what types of sources will be required to meet a particular requested power amount. Any number and variety of other parameters can be implemented in different ways at the service provider's discretion and are considered to be within the scope of the present disclosure.

The repository of vehicle information 1320 can comprise information for one or more vehicles defined by the service provider through the configuration and/or administration component. The information stored in the repository of vehicle information 1320 can comprise values for variables defined in the calculations or actions of the rules. In other cases, the information can comprise switches, flags, or other values for the conditions of the rules. For example, vehicle information may define a type of equipment, e.g., a battery type, suitable for use in a particular one or more vehicles, power usage or requirements of that vehicle in operation, and/or other information. The vehicle specific information can also be used when the rules are applied in order to select or determine appropriate power sources to meet a requested amount of power.

The rules engine 1330 can then determine power sources required to meet a requested amount of power based on applying the management rules stored in the repository maintenance management rules 1310 and using the set of service configuration parameters stored in the repository of configuration parameters 1315 and the set of vehicle information stored in the repository of vehicle information 1320. That is, once the variables of the rules are populated with the values defined in the service configuration parameters and/or the vehicle information, the rules can be executed by the rules engine 1330 and the actions defined for the rules can be performed by the rules engine 1330 based on the populated conditions. These actions comprise calculations to select or determine power sources required to meet a particular requested amount of power for one or more vehicles.

The resulting information and/or instructions indicating, for example, type of power source, number of power sources, terms of the license, etc. can be provided from the rules engine 1330 to the licensing and/or provisioning component 1335 that can then manage the process of providing the determined power sources to the vehicle. Additionally or alternatively, the information can be sent by the licensing and/or provisioning component 1335 to the vehicle or other system, for example, via a cellular or other wireless connection.

Figure 14:
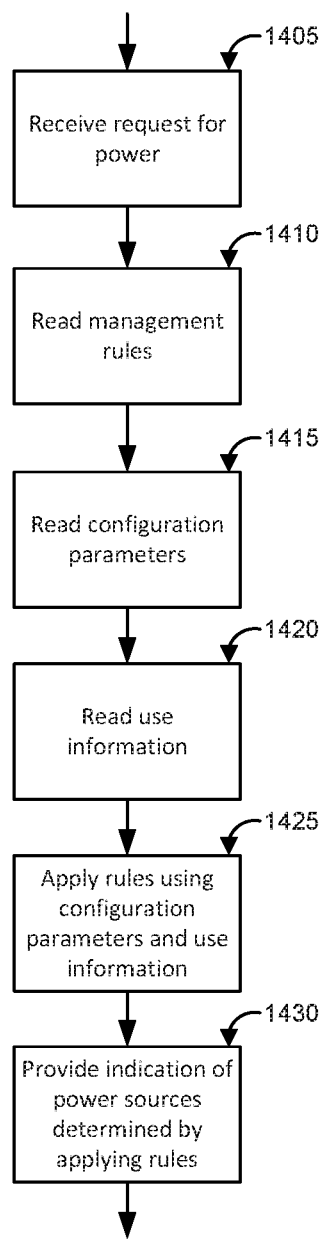
FIG. 14 is a flowchart illustrating an exemplary process for applying management rules to manage provisioning an amount of power for one or more vehicles according to one embodiment of the present disclosure.

FIG. 14 is a flowchart illustrating an exemplary process for applying management rules to manage provisioning an amount of power for one or more vehicles according to one embodiment of the present disclosure. As illustrated in this example, provisioning an amount of power for one or more vehicles can comprise receiving 1405, at a service provider system and over a communications network, a request indicating a requirement for an amount of power for the one or more vehicles. The request can indicate the requirement for the amount of power for the one or more vehicles individually or in total. The service provider system can read 1410 a set of management rules from one or more databases. The service provider system can also read 1415 a set of service configuration information and read 1420 a set of vehicle specific information for the one or more vehicles from one or more databases. For example, the set of service configuration information comprises terms of a license agreement. Additionally or alternatively, the set of vehicle specific information for the one or more vehicles can comprise information identifying a type of power source used by each of the one or more vehicles. The service provider system can determine one or more power sources to meet the requirement for the amount of power for the one or more vehicles based on applying 1425 the management rules and using the set of service configuration information and the set of vehicle information and provide 1430, over the communications network, an indication of the determined power sources.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a method for provisioning an amount of power for one or more vehicles, the method comprising: receiving, at a service provider system and over a communications network, a request indicating a requirement for an amount of power for the one or more vehicles, the request indicating the requirement for the amount of power for the one or more vehicles individually or in total; reading, by the service provider system, a set of management rules from one or more databases; reading, by the service provider system, a set of service configuration information from one or more databases; reading, by the service provider system, a set of vehicle specific information for the one or more vehicles from one or more databases; determining, by the service provider system, one or more power sources to meet the requirement for the amount of power for the one or more vehicles based on applying the management rules and using the set of service configuration information and the set of vehicle information; and providing, from the service provider system over the communications network, an indication of the determined power sources.

Aspects of the method include wherein the one or more vehicles comprises a plurality of vehicles.

Aspects of the method include wherein the request for the indicates the requirement for the amount of power for the plurality of vehicles in total.

Aspects of the method include wherein the requirement for the amount of power for the plurality of vehicles in total is expressed in terms of a total distance travelled by the plurality of vehicles.

Aspects of the method include wherein the set of service configuration information comprises terms of a license agreement.

Aspects of the method include wherein the set of vehicle specific information for the one or more vehicles comprises information identifying a type of power source used by each of the one or more vehicles.

Aspects of the method include wherein the power sources comprise batteries.

Embodiments include a system comprising a processor and a memory coupled with and readable by the processor and storing therein a set of instructions which, when executed by the processor, causes the processor to provision an amount of power for one or more vehicles, the method comprising: receiving, over a communications network, a request indicating a requirement for an amount of power for the one or more vehicles, the request indicating the requirement for the amount of power for the one or more vehicles individually or in total; reading a set of management rules from one or more databases; reading a set of service configuration information from one or more databases; reading a set of vehicle specific information for the one or more vehicles from one or more databases; determining one or more power sources to meet the requirement for the amount of power for the one or more vehicles based on applying the management rules and using the set of service configuration information and the set of vehicle information; and providing, over the communications network, an indication of the determined power sources.

Aspects of the above system include wherein the one or more vehicles comprises a plurality of vehicles.

Aspects of the above system include wherein the request for the indicates the requirement for the amount of power for the plurality of vehicles in total.

Aspects of the above system include wherein the requirement for the amount of power for the plurality of vehicles in total is expressed in terms of a total distance travelled by the plurality of vehicles.

Aspects of the above system include wherein the set of service configuration information comprises terms of a license agreement.

Aspects of the above system include wherein the set of vehicle specific information for the one or more vehicles comprises information identifying a type of power source used by each of the one or more vehicles.

Aspects of the above system include wherein the power sources comprise batteries.

Embodiments include a non-transitory computer-readable medium comprising a set of instructions stored thereon which, when executed by a processor, causes the processor to provision an amount of power for one or more vehicles by: receiving, at a service provider system and over a communications network, a request indicating a requirement for an amount of power for the one or more vehicles, the request indicating the requirement for the amount of power for the one or more vehicles individually or in total; reading, by the service provider system, a set of management rules from one or more databases; reading, by the service provider system, a set of service configuration information from one or more databases; reading, by the service provider system, a set of vehicle specific information for the one or more vehicles from one or more databases; determining, by the service provider system, one or more power sources to meet the requirement for the amount of power for the one or more vehicles based on applying the management rules and using the set of service configuration information and the set of vehicle information; and providing, from the service provider system over the communications network, an indication of the determined power sources.

Aspects of the above non-transitory computer-readable medium include wherein the one or more vehicles comprises a plurality of vehicles.

Aspects of the above non-transitory computer-readable medium include wherein the request for the indicates the requirement for the amount of power for the plurality of vehicles in total.

Aspects of the above non-transitory computer-readable medium include wherein the requirement for the amount of power for the plurality of vehicles in total is expressed in terms of a total distance travelled by the plurality of vehicles.

Aspects of the above non-transitory computer-readable medium include wherein the set of service configuration information comprises terms of a license agreement.

Aspects of the above non-transitory computer-readable medium include wherein the set of vehicle specific information for the one or more vehicles comprises information identifying a type of power source used by each of the one or more vehicles.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A method for provisioning an amount of power for one or more vehicles, the method comprising:
receiving, at a service provider system and over a communications network, a request indicating a requirement for an amount of power for the one or more vehicles, the request indicating the requirement for the amount of power for the one or more vehicles individually or in total;
reading, by the service provider system, a set of management rules from one or more databases;
reading, by the service provider system, a set of service configuration information from one or more databases;
reading, by the service provider system, a set of vehicle specific information for the one or more vehicles from one or more databases;
determining, by the service provider system, one or more power sources to meet the requirement for the amount of power for the one or more vehicles based on applying the management rules and using the set of service configuration information and the set of vehicle information;
providing, from the service provider system over the communications network to a controller of a battery exchange facility, an indication of the determined power sources; and
operating, by the controller of the battery exchange facility, equipment of the battery exchange facility to affect a battery exchange on the one or more vehicles based on the indication of the determined power sources.

2. The method of claim 1, wherein the one or more vehicles comprises a plurality of vehicles.

3. The method of claim 2, wherein the request indicates the requirement for the amount of power for the plurality of vehicles in total.

4. The method of claim 3, wherein the requirement for the amount of power for the plurality of vehicles in total is expressed in terms of a total distance travelled by the plurality of vehicles.

5. The method of claim 1, wherein the set of service configuration information comprises terms of a license agreement.

6. The method of claim 1, wherein the set of vehicle specific information for the one or more vehicles comprises information identifying a type of power source used by each of the one or more vehicles.

7. The method of claim 1, wherein the power sources comprise batteries.

8. A system comprising:
a processor; and
a memory coupled with and readable by the processor and storing therein a set of instructions which, when executed by the processor, causes the processor to provision an amount of power for one or more vehicles, the method comprising:
receiving, over a communications network, a request indicating a requirement for an amount of power for the one or more vehicles, the request indicating the requirement for the amount of power for the one or more vehicles individually or in total;
reading a set of management rules from one or more databases;
reading a set of service configuration information from one or more databases;
reading a set of vehicle specific information for the one or more vehicles from one or more databases;
determining one or more power sources to meet the requirement for the amount of power for the one or more vehicles based on applying the management rules and using the set of service configuration information and the set of vehicle information; and
providing, from the service provider system over the communications network to a controller of a battery exchange facility, an indication of the determined power sources and wherein the controller of the battery exchange facility operates equipment of the battery exchange facility to affect a battery exchange on the one or more vehicles based on the indication of the determined power sources.

9. The system of claim 8, wherein the one or more vehicles comprises a plurality of vehicles.

10. The system of claim 9, wherein the request indicates the requirement for the amount of power for the plurality of vehicles in total.

11. The system of claim 10, wherein the requirement for the amount of power for the plurality of vehicles in total is expressed in terms of a total distance travelled by the plurality of vehicles.

12. The system of claim 8, wherein the set of service configuration information comprises terms of a license agreement.

13. The system of claim 8, wherein the set of vehicle specific information for the one or more vehicles comprises information identifying a type of power source used by each of the one or more vehicles.

14. The system of claim 8, wherein the power sources comprise batteries.

15. A non-transitory computer-readable medium comprising a set of instructions stored thereon which, when executed by a processor, causes the processor to provision an amount of power for one or more vehicles by:
receiving, at a service provider system and over a communications network, a request indicating a requirement for an amount of power for the one or more vehicles, the request indicating the requirement for the amount of power for the one or more vehicles individually or in total;
reading, by the service provider system, a set of management rules from one or more databases;
reading, by the service provider system, a set of service configuration information from one or more databases;
reading, by the service provider system, a set of vehicle specific information for the one or more vehicles from one or more databases;
determining, by the service provider system, one or more power sources to meet the requirement for the amount of power for the one or more vehicles based on applying the management rules and using the set of service configuration information and the set of vehicle information;
providing, from the service provider system over the communications network to a controller of a battery exchange facility, an indication of the determined power sources; and
operating, by the controller of the battery exchange facility, equipment of the battery exchange facility to affect a battery exchange on the one or more vehicles based on the indication of the determined power sources.

16. The non-transitory computer-readable medium of claim 15, wherein the one or more vehicles comprises a plurality of vehicles.

17. The non-transitory computer-readable medium of claim 16, wherein the request indicates the requirement for the amount of power for the plurality of vehicles in total.

18. The non-transitory computer-readable medium of claim 17, wherein the requirement for the amount of power for the plurality of vehicles in total is expressed in terms of a total distance travelled by the plurality of vehicles.

19. The non-transitory computer-readable medium of claim 15, wherein the set of service configuration information comprises terms of a license agreement.

20. The non-transitory computer-readable medium of claim 15, wherein the set of vehicle specific information for the one or more vehicles comprises information identifying a type of power source used by each of the one or more vehicles.

* * * * *